United States Patent
Eilers et al.

(10) Patent No.: US 9,039,623 B2
(45) Date of Patent: May 26, 2015

(54) COMPOUND SCANNING HEAD FOR AN ULTRASONIC SCANNING APPARATUS

(75) Inventors: George J. Eilers, Evergreen, CO (US); John D. Watson, Evergreen, CO (US)

(73) Assignee: ArcScan, Inc., Morrison, CO (US)

( * ) Notice: Subject to any disclaimer, the term of this patent is extended or adjusted under 35 U.S.C. 154(b) by 515 days.

(21) Appl. No.: 12/475,322

(22) Filed: May 29, 2009

(65) Prior Publication Data

US 2010/0004538 A1 Jan. 7, 2010

Related U.S. Application Data

(60) Provisional application No. 61/057,120, filed on May 29, 2008, provisional application No. 61/084,115, filed on Jul. 28, 2008.

(51) Int. Cl.
*A61B 8/00* (2006.01)
*A61B 8/10* (2006.01)

(52) U.S. Cl.
CPC ............... *A61B 8/10* (2013.01); *A61B 8/4461* (2013.01)

(58) Field of Classification Search
USPC ......... 600/407, 411, 437, 439, 441, 444, 445, 600/452, 459; 607/69, 70, 71, 72, 76, 141
See application file for complete search history.

(56) References Cited

U.S. PATENT DOCUMENTS

| | | |
|---|---|---|
| 3,371,660 A | 3/1968 | Benson |
| 3,821,891 A | 7/1974 | Collins et al. |
| 3,997,793 A | 12/1976 | Rogers et al. |
| 4,114,214 A | 9/1978 | VonHeck |
| 4,154,114 A | 5/1979 | Katz |
| 4,183,249 A | 1/1980 | Anderson |
| 4,206,763 A | 6/1980 | Pedersen |
| 4,227,780 A | 10/1980 | Ohta et al. |
| 4,245,250 A | 1/1981 | Tiemann |
| 4,347,213 A | 8/1982 | Rogers |
| 4,484,569 A * | 11/1984 | Driller et al. .................. 600/439 |
| 4,493,877 A | 1/1985 | Burnett |
| 4,550,607 A | 11/1985 | Maslak et al. |
| 4,564,018 A | 1/1986 | Hutchison et al. |
| 4,807,634 A | 2/1989 | Enjoji et al. |
| 4,815,047 A | 3/1989 | Hart |
| 4,817,432 A | 4/1989 | Wallace et al. |
| 4,823,801 A * | 4/1989 | Sakane .......................... 600/452 |

(Continued)

FOREIGN PATENT DOCUMENTS

| | | |
|---|---|---|
| CA | 2295431 | 7/2001 |
| CA | 2299483 | 7/2001 |

(Continued)

OTHER PUBLICATIONS

U.S. Appl. No. 12/638,661, filed Dec. 15, 2009, Eilers et al.

(Continued)

*Primary Examiner* — Unsu Jung
*Assistant Examiner* — Michael N Fisher
(74) *Attorney, Agent, or Firm* — Sheridan Ross P.C.

(57) ABSTRACT

In one embodiment, the invention is directed to an ultrasound transducer whose holding device moves along a guide track while the transducer on the end of the holding device oscillates about a known position during ultrasound transmission and receiving. In this embodiment, most refractive eye components including zonules and their connection points can be imaged.

10 Claims, 24 Drawing Sheets

(56) References Cited

U.S. PATENT DOCUMENTS

| | | | |
|---|---|---|---|
| 4,858,124 A | 8/1989 | Lizzi et al. | |
| 4,858,613 A * | 8/1989 | Fry et al. | 600/439 |
| 4,930,512 A | 6/1990 | Henriksen et al. | |
| 4,932,414 A | 6/1990 | Coleman et al. | |
| 5,029,587 A | 7/1991 | Baba et al. | |
| 5,079,786 A | 1/1992 | Rojas | |
| 5,103,517 A | 4/1992 | Krouskop | |
| 5,116,114 A | 5/1992 | Nakamura et al. | |
| 5,293,871 A | 3/1994 | Reinstein et al. | |
| 5,331,962 A * | 7/1994 | Coleman et al. | 600/444 |
| 5,369,454 A | 11/1994 | Reinstein et al. | |
| 5,387,180 A | 2/1995 | Lehmer | |
| 5,460,179 A | 10/1995 | Okunuki et al. | |
| 5,474,070 A | 12/1995 | Ophir et al. | |
| 5,487,388 A * | 1/1996 | Rello et al. | 600/445 |
| 5,551,432 A | 9/1996 | Iezzi | |
| 5,556,169 A | 9/1996 | Parrish et al. | |
| 5,614,099 A | 3/1997 | Hirose et al. | |
| 5,626,150 A | 5/1997 | Johnson et al. | |
| 5,626,594 A | 5/1997 | Smith | |
| 5,776,068 A | 7/1998 | Silverman et al. | |
| 5,826,583 A | 10/1998 | Wood | |
| 5,832,550 A | 11/1998 | Hauger et al. | |
| 5,855,207 A | 1/1999 | Moenning et al. | |
| 5,906,205 A | 5/1999 | Hiebert | |
| 5,966,763 A | 10/1999 | Thomas et al. | |
| 5,971,006 A | 10/1999 | Seigerschmidt | |
| 6,053,613 A | 4/2000 | Wei et al. | |
| 6,145,143 A | 11/2000 | Hicks et al. | |
| 6,154,204 A | 11/2000 | Thompson et al. | |
| 6,198,956 B1 | 3/2001 | Dunne | |
| 6,315,727 B1 | 11/2001 | Coleman et al. | |
| 6,318,372 B1 | 11/2001 | Hiebert | |
| 6,334,227 B1 | 1/2002 | Larger | |
| 6,374,439 B2 | 4/2002 | Heimbrock et al. | |
| 6,460,207 B1 | 10/2002 | Papay et al. | |
| 6,487,447 B1 | 11/2002 | Weimann et al. | |
| 6,491,637 B2 * | 12/2002 | Foster et al. | 600/452 |
| 6,574,813 B2 | 6/2003 | Bolden et al. | |
| 6,629,929 B1 | 10/2003 | Jago et al. | |
| 6,684,433 B2 | 2/2004 | Giori et al. | |
| 6,837,855 B1 * | 1/2005 | Puech | 600/452 |
| 6,868,569 B2 | 3/2005 | VanSteenburg | |
| 6,887,203 B2 | 5/2005 | Phillips et al. | |
| 6,923,767 B2 | 8/2005 | Saied et al. | |
| 6,981,417 B1 | 1/2006 | Oravecz | |
| 7,048,690 B2 | 5/2006 | Coleman et al. | |
| 7,168,116 B2 | 1/2007 | Reger et al. | |
| 7,356,905 B2 | 4/2008 | Ketterling et al. | |
| 7,451,507 B2 | 11/2008 | Brinkerhoff et al. | |
| 7,454,024 B2 | 11/2008 | Ketterling et al. | |
| 7,474,041 B2 | 1/2009 | Ketterling et al. | |
| 7,480,058 B2 | 1/2009 | Zhao et al. | |
| 7,708,342 B2 | 5/2010 | Leach | |
| 8,064,989 B2 | 11/2011 | Brown et al. | |
| 8,115,935 B2 | 2/2012 | Everett et al. | |
| 2002/0085173 A1 | 7/2002 | Schippert et al. | |
| 2002/0143252 A1 | 10/2002 | Dunne et al. | |
| 2003/0004416 A1 | 1/2003 | Phillips et al. | |
| 2003/0142269 A1 | 7/2003 | Cumming | |
| 2004/0220478 A1 | 11/2004 | Wallace et al. | |
| 2005/0120479 A1 | 6/2005 | Habashi et al. | |
| 2006/0029525 A1 | 2/2006 | Laugharn, Jr. et al. | |
| 2006/0241533 A1 | 10/2006 | Geller | |
| 2006/0288487 A1 | 12/2006 | Roleder et al. | |
| 2007/0083995 A1 | 4/2007 | Purdy et al. | |
| 2007/0239030 A1 | 10/2007 | Prager et al. | |
| 2007/0276233 A1 | 11/2007 | Besson et al. | |
| 2008/0097214 A1 * | 4/2008 | Meyers et al. | 600/459 |
| 2009/0234369 A1 | 9/2009 | Bax et al. | |
| 2010/0031448 A1 | 2/2010 | Hijkema | |
| 2010/0217125 A1 | 8/2010 | Kadokura et al. | |
| 2010/0229306 A1 | 9/2010 | Reeder et al. | |
| 2013/0072755 A1 | 3/2013 | Papania et al. | |
| 2014/0249422 A1 | 9/2014 | Eilers et al. | |

FOREIGN PATENT DOCUMENTS

| | | |
|---|---|---|
| CA | 2395203 | 7/2001 |
| CA | 2409234 | 4/2004 |
| JP | 2006-149001 | 6/2006 |

OTHER PUBLICATIONS

U.S. Appl. No. 12/754,444, filed Apr. 5, 2010, Eilers et al.
International Preliminary Report on Patentability for International Application No. PCT/US2009/045716, mailed Dec. 9, 2010.
U.S. Appl. No. 13/796,931, filed Mar. 12, 2013, Levien.
U.S. Appl. No. 13/894,741, filed May 15, 2013, Watson et al.
U.S. Appl. No. 13/937,948, filed Jul. 9, 2013, Levien et al.
Izatt et al., "Theory of Optical Coherence Tomography," Chap. 2 of "Optical Coherence Tomography Technology and Applications," Drexler and Fujimoto eds, ISBN:978-3-540-77549-2, 2008, pp. 47-72.
Reinstein et al., "Repeatability of Layered Corneal Pachymetry With the Artemis Very High Frequency Digital Ultrasound Arc-Scanner," J. Refractive Surg., vol. 26(9), 2009, original article, 6 pages.
U.S. Appl. No. 13/684,699, filed Nov. 26, 2012, Watson.
Extended Search Report for European Patent Application No. 09755795.3, dated Jan. 3, 2013 10 pages.
U.S. Appl. No. 12/347,674, filed Dec. 31, 2008, Eilers et al.
U.S. Appl. No. 12/418,392, filed Apr. 3, 2009, Eilers et al.
Binder, "SL-OCT and Ultrasound, Support the Need for New Phakic IOL Sizing Strategies", Euro Times, p. 11, Mar. 2007.
Coleman et al., "Ultrasonography of the Eye and Orbit", Second Edition, published by Lippincott Williams & Wilkins, pp. 1-186, 2006.
Ketterling, "Design and Fabrication of a 40-MHz Annular Array Transducer", IEEE Transactions on Ultrasonics, Ferroelectrics, and Frequency Control, pp. 672-681, vol. 52, No. 4, Apr. 2005.
Ketterling, "Operational Verification of a 40-MHz Annular Array Transducer", IEEE Transactions on Ultrasonics, Ferroelectrics, and Frequency Control, pp. 623-630, vol. 53, No. 3, Mar. 2006.
Mamou, "Chirp-Coded Excitation Imaging With a High-Frequency Ultrasound Annular Array", IEEE Transactions on Ultrasonics, Ferroelectrics, and Frequency Control, vol. 55, No. 2, Feb. 2008.
Pinero et al., "Equivalence, Differences Identified in Biometric Analysis", Cataract & Refractive Surgery Today, vol. 3, No. 12, pp. 46-49, Mar. 2008.
Reinstein, "Subsurface Screening for Keratoconus—Accurate Measurements of the Epithelial and Stromal Layers Aid in Diagnosis", Cataract and Refractive Surgery Today, pp. 88-89, May 2007.
Roholt, "Sizing the Visian ICL", Cataract and Refractive Surgery Today, p. 50, May 2007.
Silverman et al., "Improved System for Sonographic Imaging and Biometry of the Cornea", pp. 117-124, 1997, Imaging and Biometry of Cornea, J. Ultrasound Med. 16:117-124.
International Search Report for International (PCT) Application No. PCT/US2009/045716, mailed Jul. 16, 2009.
Written Opinion for International (PCT) Application No. PCT/US2009/045716, mailed Jul. 16, 2009.
Background of the Invention for the above-captioned application (previously provided), See specification dated May 29, 2009.
Angelson et al. "Which transducer array is best?" European Journal of Ultrasound, 1995, vol. 2., pp. 151-164.

* cited by examiner

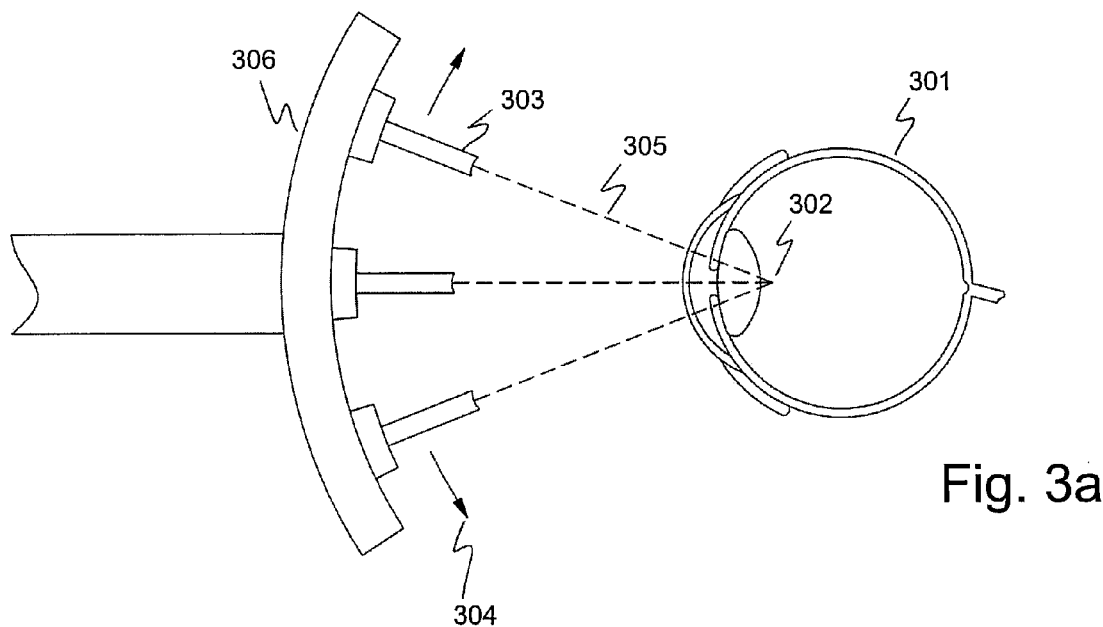
Fig. 3a
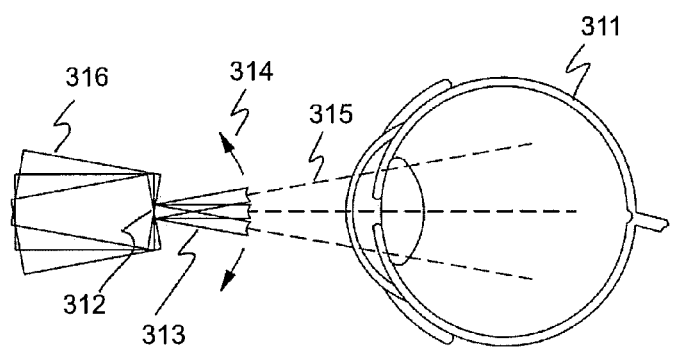
Fig. 3b
Figure 3 (Prior Art)

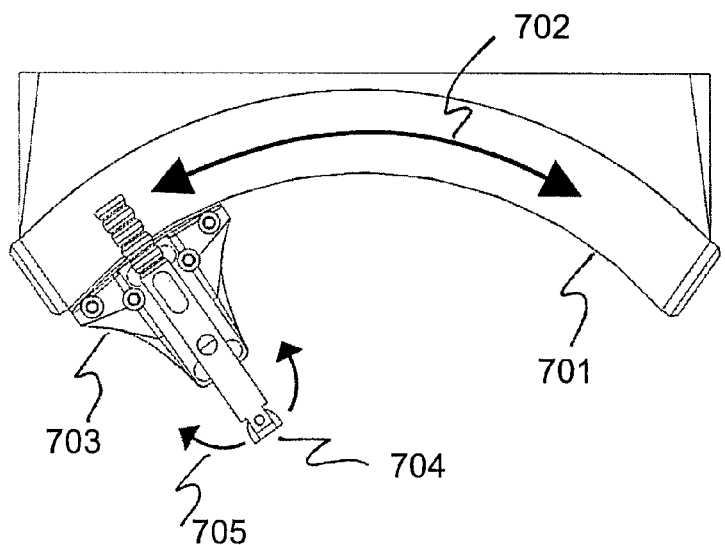
Fig. 7a
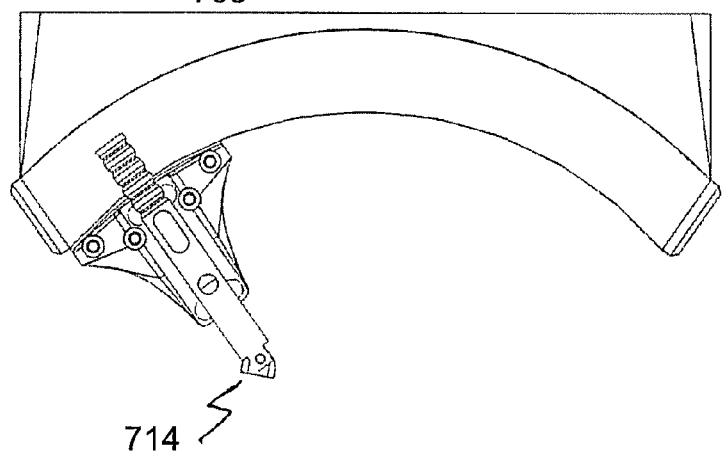
Fig. 7b
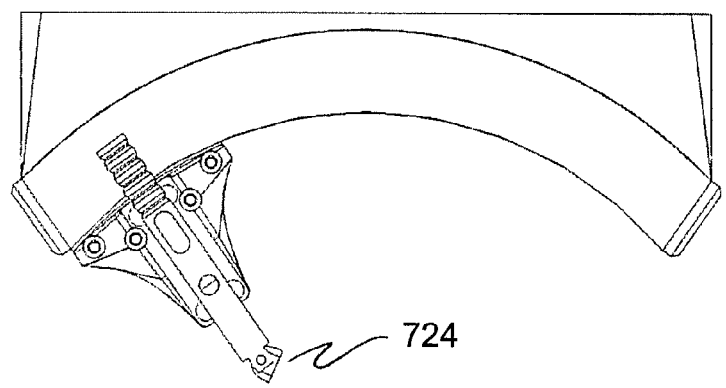
Fig. 7c
Figure 7

Fig. 12a 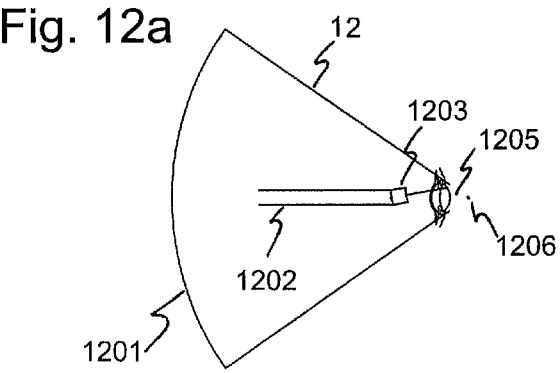 Fig. 12d 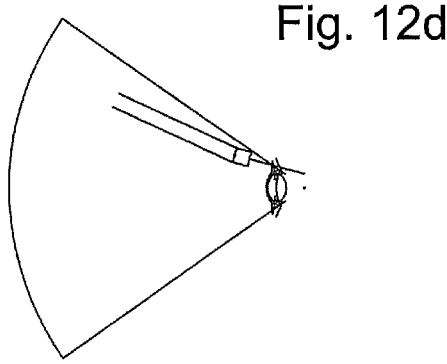
Fig. 12b 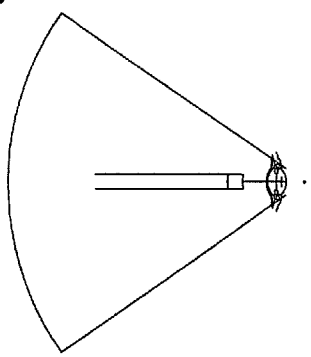 Fig. 12e 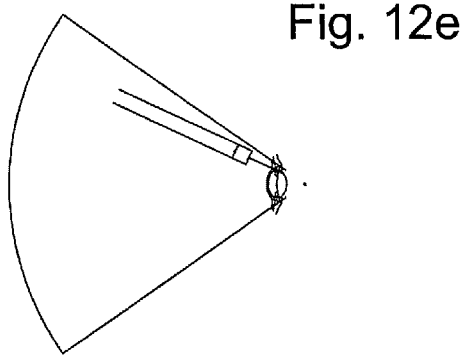
Fig. 12c 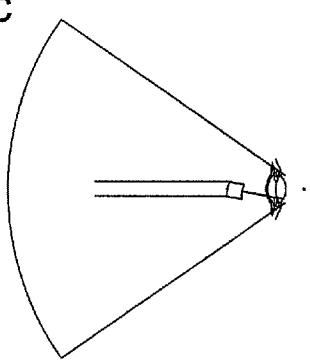 Fig. 12f 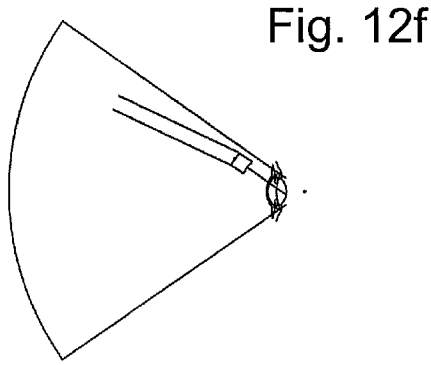
Figure 12

COMPOUND SCANNING HEAD FOR AN ULTRASONIC SCANNING APPARATUS

CROSS REFERENCE TO RELATED APPLICATION

The present application claims the benefits, under 35 U.S.C. §119(e), of U.S. Provisional Application Ser. No. 61/057,120 entitled "Compound Scanning Head for an Ultrasonic Scanning Apparatus", filed May 29, 2008 and U.S. Provisional Application Ser. No. 61/084,115 entitled "Compound Scanning Head for an Ultrasonic Scanning Apparatus", filed Jul. 28, 2008, both of which are incorporated herein by these references.

FIELD

The present invention relates generally to ultrasonic imaging of biological materials such as the cornea and natural lens of the eye and in particular relates to an ultrasonic scanning device that combines a sector scanning head with an arc scanning system.

BACKGROUND

Ultrasonic imaging of the cornea and lens capsule presents a problem not generally encountered in other types of tissue. The corneal and lens capsule surfaces are necessarily smoothly curved in order to perform their optical function of focusing light rays. Because the cornea and lens structures are smooth and regular, ultrasonic energy is reflected directly back to that transducer when the beam is aligned perpendicular to the corneal or lens surface. This kind of reflective property is call specular reflection. Because of the specular property of corneal and lens surfaces, it will be appreciated that special care must be taken to align the transducer so that the emitted acoustic pulses impinge normally on the surface of the cornea or the lens surface of interest at each position from which an element of the image is to be formed.

In the case of the cornea, ultrasonic imaging of large portions of the cornea can be accomplished by scanning the transducer along the corneal surface while continually adjusting the alignment of the transducer to provide a beam that is always directed approximately through the cornea's center of curvature. Corneal imaging and measurement of corneal dimensions require that the scanning motion of the transducer be smooth and precisely aligned. Departures of the transducer position as small as 5 microns from a circular path or of the beam's direction from the center of curvature can significantly degrade the resulting image. Mechanisms for performing the requisite scan alignment are described in U.S. Pat. Nos. 5,331,962; 6,887,203; and U.S. patent application Ser. No. 12/347,674.

While ultrasonic imaging may be used by ophthalmologists for quantitative analysis of laser refractive surgery, it may also be used for implantation of corneal and phakic lenses, implantation of intraocular lenses including accommodative lenses and specialty procedures such as glaucoma and cataract treatment. The use of ultrasonic imaging of important features of the eye for lens implantation is discussed, for example, in U.S. Pat. No. 7,048,690. This patent does not include techniques for imaging the posterior surface of the lens capsule and so cannot be used to compute the volume of a lens capsule.

The components of the eye in front of the iris can be mapped and measured by both optical and acoustic means to a high degree of accuracy. Except for features near the optical axis, the components of the eye behind the iris cannot be imaged optically but can be imaged by acoustic techniques. In particular, the region of the lens capsule where the anterior and posterior surfaces meet and the zonules that attach the lens capsule to the ciliary body cannot be observed by optical systems but can be successfully imaged by high frequency (10 to 50 MHz) ultrasound devices. New procedures such as implantation of accommodative lenses may provide nearly perfect vision without spectacles or contact lenses. Implantation of accommodative lenses, if full accommodation is to have a high degree of success, requires precision measurements of, for example, the width, volume and shape of the natural lens capsule for successful lens implantation. Ultrasonic imaging can be used to provide the required accurate images of the natural lens especially where the zonules attach the lens to the ciliary muscle, all of which are well off-axis and behind the iris and therefore not accessible to optical imaging.

Ultrasonic imaging has other advantages over optical imaging devices, even in the cornea. For example, ultrasonic pulses interact on the basis of acoustic/mechanical properties with the various components of the eye whereas optical pulses may interact weakly since the eye has evolved primarily to refract but not substantially reflect or attenuate. These differing physics give rise to another advantage for acoustic imaging. Corrections due to differing acoustic velocities of the various eye components are on the order of about 1 to 10 percent whereas optical corrections for index of refraction differences are on the order of about 25 to 35 percent. This gives ultrasonic imaging an advantage for measuring such features as the angle between the iris and corneal sclera in the anterior chamber.

It must be appreciated that ultrasonic imaging requires a liquid medium to be interposed between the object being imaged and the transducer, which requires in turn that the eye, the transducer, and the path between them be at all times be immersed in a liquid medium. Concern for safety of the cornea introduces the practical requirement that the liquid medium be pure water or normal saline water solution. In either case, the mechanism or major portions of it must be submerged in water for long periods.

Typically, ultrasonic imaging practice uses a single fixed transducer which can move along an arcuate guide for both sending ultrasound pulses to and receiving echos from eye structures. It is readily demonstrated that, with this arrangement, specular surfaces only return echos along the axis of the incident beam if the incident beam is directed normally or perpendicularly to the surface. This behavior has led to the development of ultrasound imaging devices that maintain their incident beam approximately perpendicular to the corneal or lens surface as the incident ultrasound beam scans the surface. An exemplary embodiment of such a device is described in U.S. patent application Ser. No. 12/347,674 filed Dec. 31, 2008 entitled "Components for an Ultrasonic Arc Scanning Apparatus" and in U.S. patent application Ser. No. 12/418,392 filed Apr. 3, 2009 entitled "Procedures for an Ultrasonic Arc Scanning Apparatus ", both of which are incorporated herein by reference. With such a device, the incident beam scans in a plane while directing its axis through a fixed center of curvature. If that center of curvature of the arcuate guide is coincident or nearly coincident with the center of curvature of the corneal or lens surface, the incident beam will remain approximately perpendicular to the surface throughout the scan, and ultrasound reflections will be returned to the transducer from all scanned parts of the surface, allowing the formation of a complete image.

While all of the corneal surfaces have nearly the same center of curvature locally, the center of curvature may vary along the arc of the cornea. That is, the entire cornea typically does not form a perfectly circular arc. Moreover, the natural lens anterior and posterior surfaces are centered at different locations from one another and from that of the cornea. The lens surfaces also typically do not form perfectly circular arcs.

There remains, therefore, a need for an ultrasonic arc scanning method that can produce a superior and more comprehensive image of a cornea, lens and other eye components, such as the zonules that attache the lens capsule to the ciliary body, than an arc scanner with a fixed focal point such as described, for example, in U.S. patent application Ser. No. 12/418,392.

SUMMARY

These and other needs are addressed by the present invention. The various embodiments and configurations of the present invention are directed generally to ultrasonic imaging of biological materials such as the cornea and lens of the eye and in particular directed to an ultrasonic arc scanning apparatus with an independently rotatable sector scan head mounted on the carriage of an arc scanning apparatus so as to form a compound scanning head. The methods and systems disclosed below can produce multi-dimensional images of the biological materials.

In a first embodiment, an ocular imaging method is provided that includes the steps:

(a) moving a carriage along a guide track, the carriage comprising a acoustic transducer; and (b) while the carriage is positioned on the guide track, rotating, relative to the carriage, the transducer back and forth while the transducer emits acoustic signals, whereby a selected ocular feature or features are imaged.

In another embodiment, an ocular imaging system includes:

at least a first ultrasonic transducer;
a guide track; and
at least a first carriage operable to move along the guide track, the at least a first carriage comprises the at least a first ultrasonic transducer, wherein the at least a first transducer oscillates back and forth while the at least a first transducer emits ultrasonic signals, whereby a selected ocular feature is imaged.

Typically, the transducer is part of a scan head, the scan head is mounted on a scanner head mount arm, and the mount arm is secured to the carriage. Preferably, a radius of curvature of the guide track approximates a radius of curvature of a selected ocular feature.

In one configuration, a number of scan vectors are generated. The scan vectors are processed as follows:

(i) while the carriage is moving along the guide track, determining a position of the carriage along the guide track as a function of time; and (ii) determining the angular position of the transducer as a function of time.

In one configuration, a center of curvature of the arcuate guide track is set approximately at a center of curvature of the ocular feature of interest. Acoustic signals are emitted as the carriage moves along the guide track, and the ocular feature of interest is one or more of a surface or layer of a cornea, a surface of a lens, a zonule, a region of a sclera, a region of a ciliary body, an iris and a ciliary sulcus.

The operation of the transducer is generally bimodal. The transducer, in a first mode, transmits acoustic signals and, in a second mode, receives acoustic signals. While the carriage is moving along the guide track, the transducer operates in both modes at different times.

In one configuration, the transducer rotates back and forth substantially in a plane of the guide track. Typically, the transducer rotates, relative to a reference angle position, within a range of from about −25° to about +25°, rotates back and forth at a frequency ranging from about 500 to about 2,000 Hz, and is pulsed from about 8 to about 64 times per cycle of transducer rotation.

In one configuration, carriage movement along the guide track is discontinuous. In other words, the following steps are performed:

(b1) moving the carriage to a first location on the guide track;

(b2) at the first location, stopping movement of the carriage;

(b3) at the first location, emitting a first set of acoustic signals;

(b4) at the first location, receiving a second set of reflected acoustic signals; and (b5) moving to a second location on the guide track; and (b6) repeating steps (b1)-(b5) at the second location.

The above embodiments present an approach that can allow the cornea surfaces and lens surfaces to be imaged at the same time. This is of considerable value, as it reduces the time required for the scan as well as the skill required of the operator who must align the device with a patient's eye. Further, this invention can allow a more complete image of the lens or corneal surfaces by extending the lateral range of a scan. Even further, this invention can allow images to be made of the zonules and their connection points on the anterior and posterior lens surfaces and on the ciliary body. Again, this is of considerable value, as it can reduce the time required for a comprehensive scan of the anterior segment.

Alternate ultrasonic scanning configurations are also disclosed. In one such embodiment, an imaging system includes:

(a) at least a first movable carriage;

(b) a guide track engaged with the at least a first movable carriage; and (c) at least first and second ultrasound transducers, the first ultrasound transducer being positioned on the at least a first movable carriage, wherein the second ultrasound transducer is positioned at a location at or near the guide track different from a location of the at least a first carriage, and wherein the first transducer acts as an ultrasound transmitter and the second transducer as an ultrasound receiver.

In this configuration, multiple moveable transducer carriages are used on an arc scanning guide track. Each carriage is comprised of a transmitter/receiver transducer and several receiver transducers. This configuration can allow two- and three-dimensional images of eye components to be generated by tomographic techniques and does not depend on the transmitted signal reflecting approximately normally from a surface with an acoustic impedance mismatch.

In another embodiment, an imaging system is disclosed that includes:

(a) a movable carriage;

(b) an arcuate guide track engaged with the movable carriage, the arcuate guide track having a curvature approximating a curvature of a selected feature to be imaged in a patient's eye; and (c) a transducer array positioned on the carriage and comprising at least a first set of transmitter transducers and a second set of receiver transducers and wherein, in a tomographic mode and as the carriage traverses the guide track, a three dimensional image of the selected ocular feature is generated using results of scans by first and second sets of transducers.

This embodiment can permit three-dimensional images to be produced by tomographic techniques.

Finally, a method is disclosed for using a compound head ultrasonic scanner to fit, implant and verify operation of an artificial accommodating lens.

The following definitions are used herein:

An A-scan is a representation of the reflected acoustic signal amplitudes as a function of time received by an ultrasonic transducer from acoustic pulses originally emitted by the ultrasonic transducer from a known fixed position relative to an eye component.

An accommodative lens, also known as a presbyopic lens or presby lens, is an artificial intraocular lens that changes its focal distance in response to contraction of the ciliary muscle. When successfully implanted, an accommodative lens reverses presbyopia, the inability of the eye to change its focal distance from far to near.

Aligning means positioning the transducer and transducer carriage guide preferably accurately and reproducibly in space with respect to a feature of the eye component of interest (such as the center of curvature or boundary of the cornea, lens, retina, etcetera).

The anterior chamber comprises the region of the eye from the front of the eye to the iris.

The anterior segment comprises the region of the eye from the front of the eye to just beyond the back of the lens.

An aperture refers to the ultrasonic transducer face which may be planar but is commonly shaped as a concave surface so as to form a focal point at a desired location.

An arc scanner is a scanning device where the sensor moves in a substantially precise arc about the center of the area to be scanned with its beam constantly directed through a central point.

Arc scanning transducer center of curvature is the same as the center of curvature of the arc scanning guide.

Auto-centering means automatically, typically under computer control, causing centration of the arc scanning transducer with the eye component of interest.

A B-scan is processed representation of A-scan data by either or both of converting it from a time to a distance using acoustic velocities or by using grayscales which correspond to A-scan amplitudes highlight the features along the A-scan time history trace (also referred to as an A-scan vector).

A canthus is the angular junction of the eyelids at either corner of the eye where the upper and lower eyelids meet.

Centration means substantially aligning the center of curvature of the arc scanning transducer in space with the center of curvature of the eye component of interest (such as the cornea, lens, retina, etcetera) such that rays from the transducer pass through both centers of curvature. A special case is when both centers of curvature are coincident.

The ciliary body is the circumferential tissue inside the eye composed of the ciliary muscle and ciliary processes. There are three sets of ciliary muscles in the eye, the longitudinal, radial, and circular muscles. They are near the front of the eye, above and below the lens. They are attached to the lens by connective tissue called the zonule of Zinn, and are responsible for shaping the lens to focus light on the retina. When the ciliary muscle relaxes, it flattens the lens, generally improving the focus for farther objects. When it contracts, the lens becomes more convex, generally improving the focus for closer objects.

Coronal means of or relating to the frontal plane that passes through the long axis of a body. With respect to the eye or the lens, this would be the equatorial plane of the lens which also approximately passes through the nasal canthus and temporal canthus of the eye.

Fixation means having the patient focus an eye on an optical target such that the eye's optical axis is in a known spatial relationship with the optical target. In fixation, the light source is axially aligned in the arc plane with the light source in the center of the arc so as to obtain maximum signal strength such that moving away from the center of the arc in either direction results in signal strength diminishing equally in either direction away from the center.

A guide is an apparatus for directing the motion of another apparatus.

Haptics are little curved hair-like protrusions extending from the outer diameter of some types of artificial lenses. These haptics attach these lens to the ciliary muscle by protruding into the ciliary sulcus and allow the lens to accommodate in response to the action of the ciliary muscle.

An intraocular lens is an artificial lens that is implanted in the eye to take the place of the natural lens.

LASIK is a procedure performed on the cornea for correcting refractive errors, such as myopia, hyperopia, and astigmatism. Commonly, an excimer laser selectively removes tissue from the inside of the cornea, after exposing it by cutting a thin flap, so as to reshape the external shape of the cornea.

A meridian is a plane that cuts through a portion of a three-dimensional component such as the cornea or natural lens of the eye and its angle is commonly expressed relative to a horizon defined by the nasal canthus and temporal canthus of the eye.

The natural lens (also known as the aquula or crystalline lens) is a transparent, biconvex structure in the eye that, along with the cornea, helps to refract light to be focused on the retina. The lens, by changing shape, functions to change the focal distance of the eye so that it can focus on objects at various distances, thus allowing a sharp real image of the object of interest to be formed on the retina. This adjustment of the lens is known as accommodation. The lens is located in the anterior segment of the eye behind the iris. The lens is suspended in place by the zonular fibers, which attach to the lens near its equatorial line and connect the lens to the ciliary body. The lens has an ellipsoid, biconvex shape whose size and shape can change due to accommodation and due to growth during aging. The lens is comprised of three main parts: namely the lens capsule, the lens epithelium, and the lens fibers. The lens capsule forms the outermost layer of the lens and the lens fibers form the bulk of the interior of the lens. The cells of the lens epithelium, located between the lens capsule and the outermost layer of lens fibers, are generally found only on the anterior side of the lens.

Ocular means having to do with the eye or eyeball.

Ophthalmology means the branch of medicine that deals with the eye.

Optical as used herein refers to processes that use light rays.

The optical axis of the eye is the line of best fit joining the centers of curvature of the refracting surfaces (the anterior and posterior surfaces of the cornea and lens).

Pachymetery or corneal pachymetery is technically referred to as Time Domain Reflectometry ultrasound. A pulse of ultrasonic energy is sent toward the cornea and the time spacing of the returning echoes are used to arrive at corneal thickness.

Phakic intraocular lenses, or phakic lenses, are lenses made of plastic or silicone that are implanted into the eye permanently to reduce a person's need for glasses or contact lenses.

Phakic refers to the fact that the lens is implanted into the eye without removing the eye's natural lens. During phakic lens implantation surgery, a small incision is normally made in the front of the eye. The phakic lens is inserted through the incision and placed just in front of or just behind the iris.

The posterior chamber comprises the region of the eye from the back of the iris to the front of the lens.

The posterior segment comprises the region of the eye from the back of the lens to the rear of the eye comprising the retina and optical nerve.

Presbyiopia is typically caused by a loss of elasticity of the natural lens inside the eye. This occurs as part of the ageing process and, although it cannot be 'cured', it can be corrected by wearing glasses or implanting an artificial lens.

Purkinje images are reflections of objects from structure of the eye. There are at least four Purkinje images that are visible on looking at an eye. The first Purkinje image (P1) is the reflection from the outer surface of the cornea. The second Purkinje image (P2) is the reflection from the inner surface of the cornea. The third Purkinje image (P3) is the reflection from the outer (anterior) surface of the lens. The fourth Purkinje image (P4) is the reflection from the inner (posterior) surface of the lens. Unlike the others, P4 is an inverted image. The first and fourth Purkinje images are used by some eye trackers, devices to measure the position of an eye. Purkinje images are named after Czech anatomist Jan Evangelista Purkyně (1787-1869).

Refractive means anything pertaining to the focusing of light rays by the various components of the eye.

Registration means aligning.

Sector scanner is an ultrasonic scanner that sweeps out a sector like a radar. The swept area is pie-shaped with its central point typically located near the face of the ultrasound transducer.

A specular surface means a mirror-like surface that reflects either optical or acoustic waves. For example, an ultrasound beam emanating from a transducer will only be reflected directly back to that transducer when the beam is aligned perpendicular to a specular surface.

The ciliary sulcus is the groove between the iris and ciliary body. The scleral sulcus is a slight groove at the junction of the sclera and cornea.

A track is an apparatus along which another apparatus moves.

Ultrasonic means sound that is above the human ear's upper frequency limit. When used for imaging an object like the eye, the sound passes through a liquid medium, and its frequency is many orders of magnitude greater than can be detected by the human ear. For high-resolution acoustic imaging in the eye, the frequency is typically in the approximate range of about 5 to about 80 MHz.

A vector refers to a single acoustic pulse and its multiple reflections from various eye components. An A-scan is a representation of this data which is typically rectified.

The visual axis of the eye is the line joining the object of interest and the fovea and which passes through the nodal points.

Zonules are tension-able ligaments extending from near the outer diameter of the crystalline lens. The zonules attach the lens to the ciliary body which allows the lens to accommodate in response to the action of the ciliary muscle.

As used herein, "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

BRIEF DESCRIPTION OF THE DRAWINGS

FIG. 3 illustrates two different types of scanning strategies for ultrasonic scanners.

FIG. 7 is a schematic of a compound scanning head of the present invention.

FIG. 12 shows a sequence of scans with a compound scanner head.

FIG. 13 shows an up close schematic of FIG. 12a.

DETAILED DESCRIPTION

The present invention discloses a configuration of ultrasonic scanner having a compound scan head mechanism that combines an arc scan head positioning mechanism, an arc guide track with moveable carriage, a transducer body mount secured to the moveable carriage and a sector scan head that is mounted on the end of the transducer body mount where the sector scan head, which contains the ultrasonic transducer, is independently rotatable within the plane of the arc guide track. In the example used to illustrate this invention, the transducer body and its independently rotatable ultrasonic transducer head are mounted on a transducer carriage that moves along a circularly curved guide track. The carriage is guided by the track so that the transducer beam axis rotates back and forth in the plane of the arc track while the axis of the transducer body mount is always directed toward a fixed center point (the center of curvature of the arc guide track) regardless of the carriage's position along the track. As can be appreciated, the guide track need not be a circularly curved guide track but can be a guide track with a different curvature or even a linear track.

As disclosed in U.S. patent application Ser. Nos. 12/347,674 and 12/418,392, a preferred embodiment incorporates a transducer carriage that has a linear motor and a fluidic bearing that allows a smooth motion of the carriage along the arc guide track. Also in the preferred embodiment, there is a position encoder, preferably incremental and magnetic, borne by the track and the carriage, that allows external circuitry to sense the position of the carriage along the track. The positional information is used to trigger the sending of ultrasonic pulses so as to provide precise and accurate position of the carriage along the arc guide track in relation to each emitted acoustic pulse wave train at all times. In the present invention, the exact angular position of the rotatable transducer head is also required so that the precise and accurate position of each A-scan vector will be known in space and time. This angular information can be determined by any number of well-known position encoder means.

Ultrasonic Scanning Principles

Figure 1:
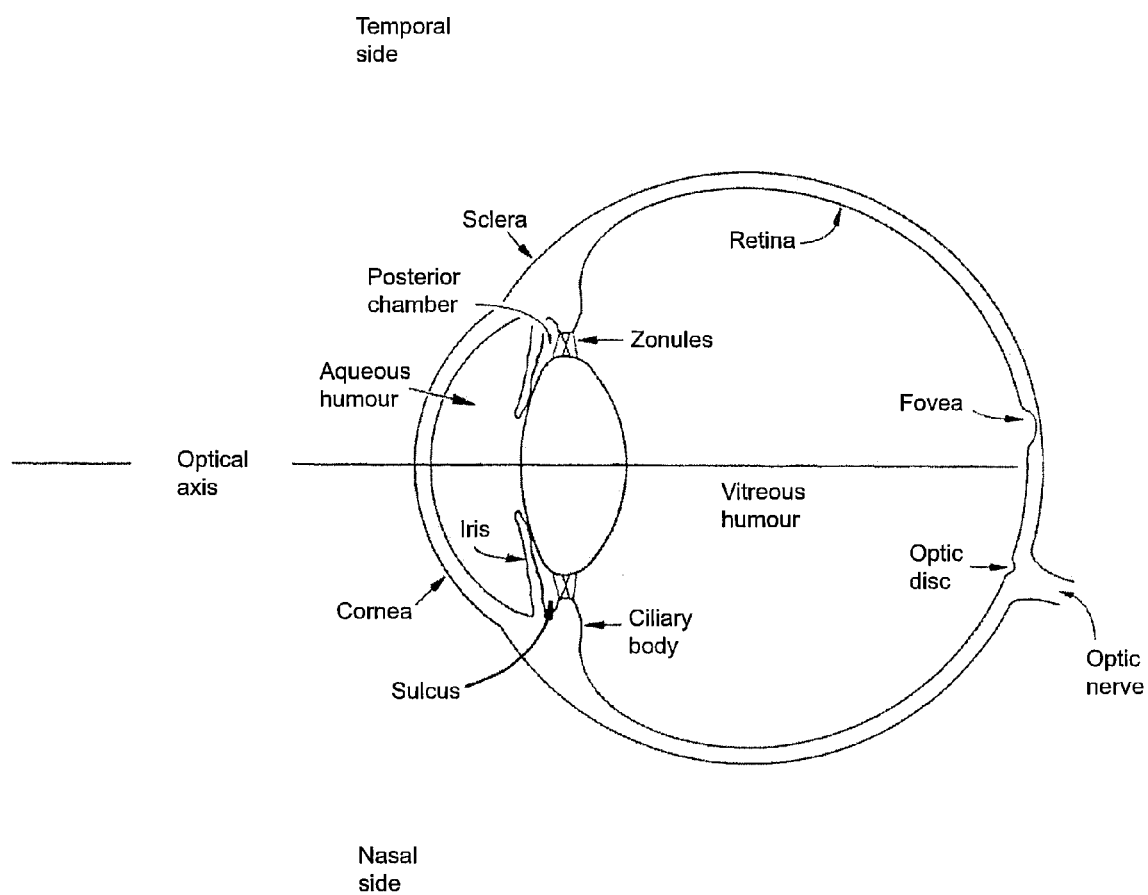
FIG. 1 is a schematic of the main elements of a human eye.

FIG. 1 is a schematic of the main elements of a human eye taken from "Optics of the Human Eye", D. A. Atchison, G. Smith, Robert Stevenson House, Edinburgh, ISBN 0 7506 3775 7, first printed in 2000. This figure shows schematically the attachment of the lens to the ciliary body by the zonules. Also shown is the ciliary sulcus, a groove which may be used in certain types of artificial accommodating lenses for referencing purposes or for securing the lens to the ciliary body. The principal refracting components are the cornea, iris and lens. The cornea, which is optically transparent, is located at the front of the eye and encloses the front side of the anterior chamber. The iris separates the anterior chamber from the posterior chamber. The front of the lens encloses the back side of the posterior chamber. The natural lens sits directly behind the iris. Only the central part of the lens, which is behind the pupil, can be seen optically The region between the anterior surface of the cornea and the and posterior surface of the lens forms the anterior segment of the eye. The main volume or posterior segment of the eye lies behind the lens, with the retina and optical nerve at the rear of the posterior segment of the eye. The composition of the eye's aqueous and vitreous humour are very close to that of water with a density of about 1,000 kg/m$^3$ and this allows the eye to be a very good medium for the transmission of acoustic energy.

Optical means are suitable for viewing the anterior chamber and for viewing along the entire central axis of the eye. However, optical means cannot be used to view the portions of the posterior chamber lying immediately behind the iris, which includes the suspensory ligaments (called zonules), ciliary sulcus and ciliary body. However, the eye components that cannot be viewed optically, can be viewed with high-frequency acoustic energy. As is well-known, acoustic frequencies in the ultrasonic range of about 10 MHz to about 60 MHz can be used to provide very high resolution images of, for example, the cornea and the lens and even foreign bodies in the vitreous humour.

Some of the typical dimensions of the human eye in millimeters, which apply at least along or near the optical axis, are:
Thickness of cornea=0.5 mm
Radius of curvature anterior cornea surface=7.7 mm
Radius of curvature posterior cornea surface=6.8 mm
Distance from the front of the cornea to the front of the lens=3.3 mm
Thickness of lens=3.5 mm
Radius of curvature anterior lens surface=11 mm
Radius of curvature posterior lens surface=−6.0 mm
Equatorial diameter of lens=8.5 mm to 10 mm
Distance from the rear of the lens to the front of the retina=16 mm These are representative dimensions of the relaxed eye. The distance from the front of the cornea to the front of the lens along the axis and the thickness of lens along the axis depend upon accommodation. These values were taken from "Optics of the Human Eye" cited above.

Figure 2:
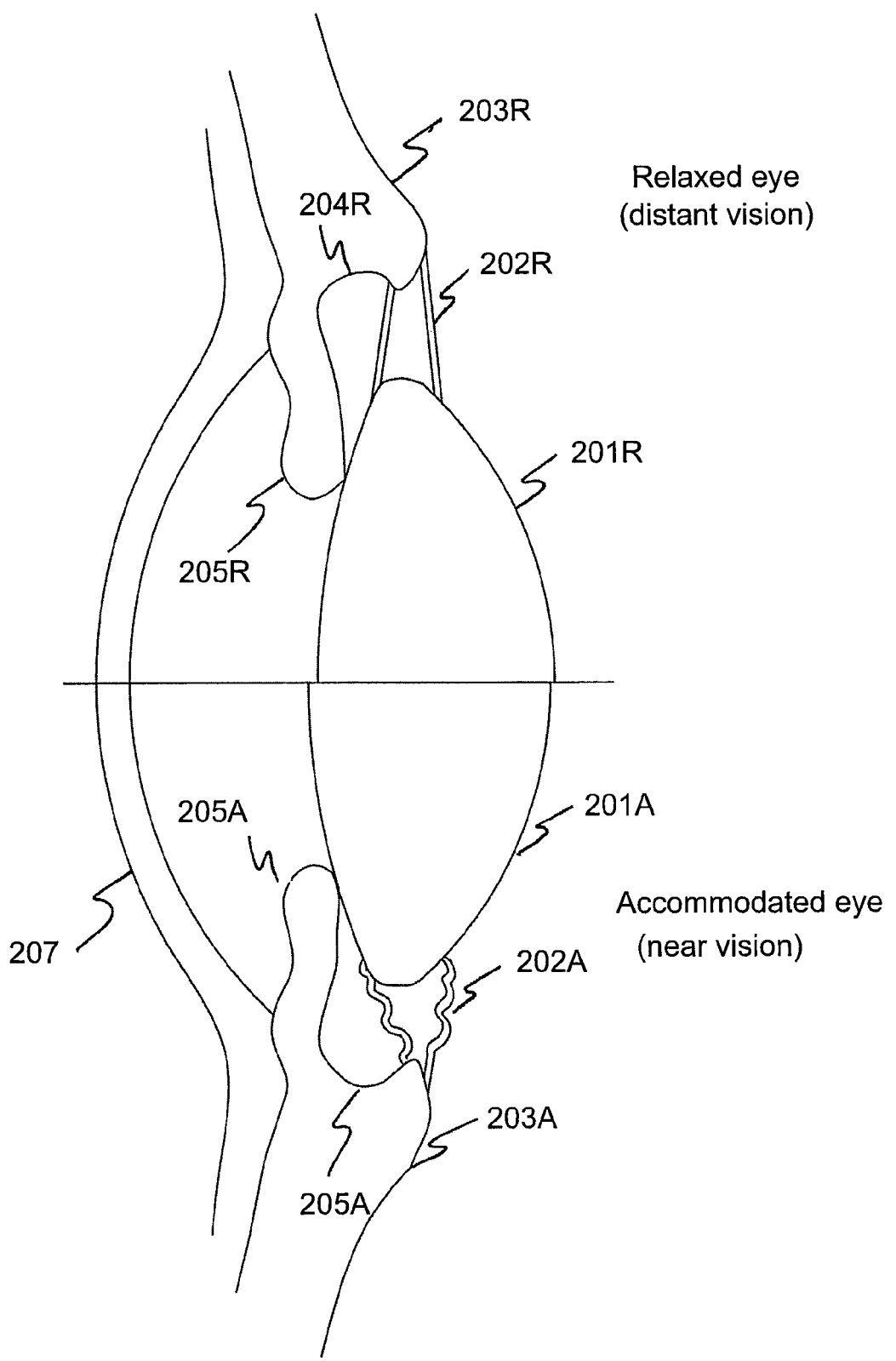
FIG. 2 is a schematic representation of an accommodating lens.

FIG. 2 is a schematic representation of an accommodating natural lens. For explanatory purposes, the upper half of the eye is shown in relaxed mode (the ciliary muscle is relaxed and the zonules are tensioned) which is associated with distant vision. The lower half of the eye is shown in accommodated mode (the ciliary muscle contracts decreasing tension on the zonules) which is associated with near vision. In accommodated mode, the lens is moved slightly forward and the lens shape is changed slightly, becoming slightly thicker along its optical axis. The approximate lens shape in relaxed mode 201R and in accommodative mode 201A are shown. When the ciliary muscle contracts 203A, tension in the zonules is reduced and this allows the lens to accommodate which is appropriate for near vision. When the ciliary muscle expands 203R, tension in the zonules is increased and this allows the lens to relax which is appropriate for distant vision.

Also shown in FIG. 2 are the cornea 207; the ciliary body in relaxed mode 203R and accommodated mode 204A; the iris in relaxed mode 205R and accommodated mode 205A; the ciliary sulcus in relaxed mode 204R and accommodated mode 204A.

In sizing a lens replacement, it is of great value to be able to measure where the zonules attach to the lens and the ciliary body. A first set of zonules attach to the anterior surface of the lens and a second set attach to the posterior surface of the lens. Depending on the state of accommodation, the zonules can be stretched tight when the ciliary muscle is relaxed or they can be loose when the ciliary muscle is contracted. Thus the zonules can be difficult to image with acoustic pulses. Imaging the zonules can be accomplished by an imaging system with a transducer head that can be aimed with accuracy and precision in a complex way such as is possible with the compound head of the present invention.

Once an accommodating lens is implanted or its natural accommodating action restored by, for example, injection of softening agents, such a scanner can then be set up to target the region where the lens and the ciliary muscle are located and/or the central portion of the lens. The scanner of the present invention can then be used to generate a series of images that show the ciliary muscle and lens attachment means responding to the patient focusing at different distances and that show the movement of the central portion of the lens (anterior surface, posterior surface or both) responding to the patient focusing at different distances. If the lens does not accommodate correctly, these images can be used to diagnose the problem areas such as, for example, failure of the haptics of an artificial accommodating lens to attach properly to the ciliary body, or failure of either anterior apex or posterior apex to move as the eye attempts to change focus.

These procedures can be repeated from time to time with the scanner of the present invention to detect any movement or degradation of the lens, be it a softened natural lens or an artificial accommodating lens.

FIG. 3 illustrates two different types of prior art scanning strategies for ultrasonic scanners capable of imaging most regions of the interior of an eye. FIG. 3a illustrates the arc scanning principle for producing an ultrasonic scan of a component of an eye 301. In this type of scanner, which is described, for example, in U.S. Pat. Nos. 7,048,690; 6,887,203; 6,491,637; 6,315,727; 5,33,962; 5,293,871; and U.S. patent application Ser. No. 12/347,674, a transducer is moved in an arc whose center of curvature is set approximately at the center of curvature of the eye surface of interest. In FIG. 3a, an ultrasonic transducer 303 is shown in a sequence of positions with the center of curvature of the arc guide 306 at approximately the center of curvature 302 of the cornea (the radii of curvature and the centers of curvature of the anterior and posterior surfaces of the cornea are very close to each other). The transducer 303 is moved in an arc as shown to produce many acoustic echoes (represented as rays 305) as it moves along the arc guide which can then be combined to form a cross-sectional image of the eye features of interest.

FIG. 3b illustrates the sector scanning principle for producing an ultrasonic image of a particular location with an eye 311. In this type of hand-held scanner, which is described, for example, in U.S. Pat. No. 6,198,956 an ultrasonic transducer 313 is shown being oscillated about a fixed position 312 so as to produce many acoustic echoes (represented as rays 315). These echoes can then be combined to form of a localized region of interest within the eye. The scanning principle illustrated in this figure is called sector scanning.

In both the arc and sector ultrasonic scanners, the transducer acts as both the transmitter and receiver of acoustic signals. The transducer emits a short acoustic pulse and then receives the reflected acoustic signal. This technique is described, for example, in U.S. Pat. No. 5,293,871 and in "Ultrasonography of the Eye and Orbit", Second Edition, Coleman et al, published by Lippincott Williams & Wilkins, 2006.

A sector scanner can be used to measure the thickness of an eye component such as, for example, the thickness of the cornea or the thickness of the lens along the optical axis. A sector scanner cannot be used to measure the length of specular features that extend laterally, such as, for example, the length of a LASIK scar, because only that small portion of the cornea that is perpendicular to the acoustic beam and reflects acoustic energy back to the transducer is visible to a sector scanner. With a sector scanner, the patient is typically required to be supine and the scanner is pressed lightly against the cornea.

An arc scanner, on the other hand, can be used to measure the thickness of an eye component such as, for example, the thickness of the cornea or the thickness of a lens as well as to measure the length of specular features that extend laterally, such as, for example, the length of a LASIK scar or the lateral length of a natural or implanted lens. In an arc scanner, the patient is typically looking downward at approximately 45 degrees from horizontal. This is a preferred position for an arc scanning device such as described in U.S. patent application Ser. Nos. 12/347,674 and 12/418,392 cited above.

Both arc and sector scanners are discussed on page 35 of "Ultrasonography of the Eye and Orbit" cited above.

As will be described below, the present invention discloses a compound scanning head in which elements of arc scanners and sector scanners are combined in a way that results in superior images and an extension of lateral range.

Scan Head Positioning Apparatus and Position Sensing

The function of a scan head positioning apparatus in a conventional arc scanning device is to position the arc scanning head assembly and ultrasonic transducer so that the transducer head can move continuously on an arc guide that is positioned such that its center of curvature is at the approximate center of curvature of the eye component to be scanned. A successful scan often requires that the radius of curvature of the arc assembly approximately match the radius of curvature of the eye component of interest and that the scan head positioning apparatus be accurately positioned to take advantage of the precision of a high frequency ultrasonic pulse.

Figure 4:
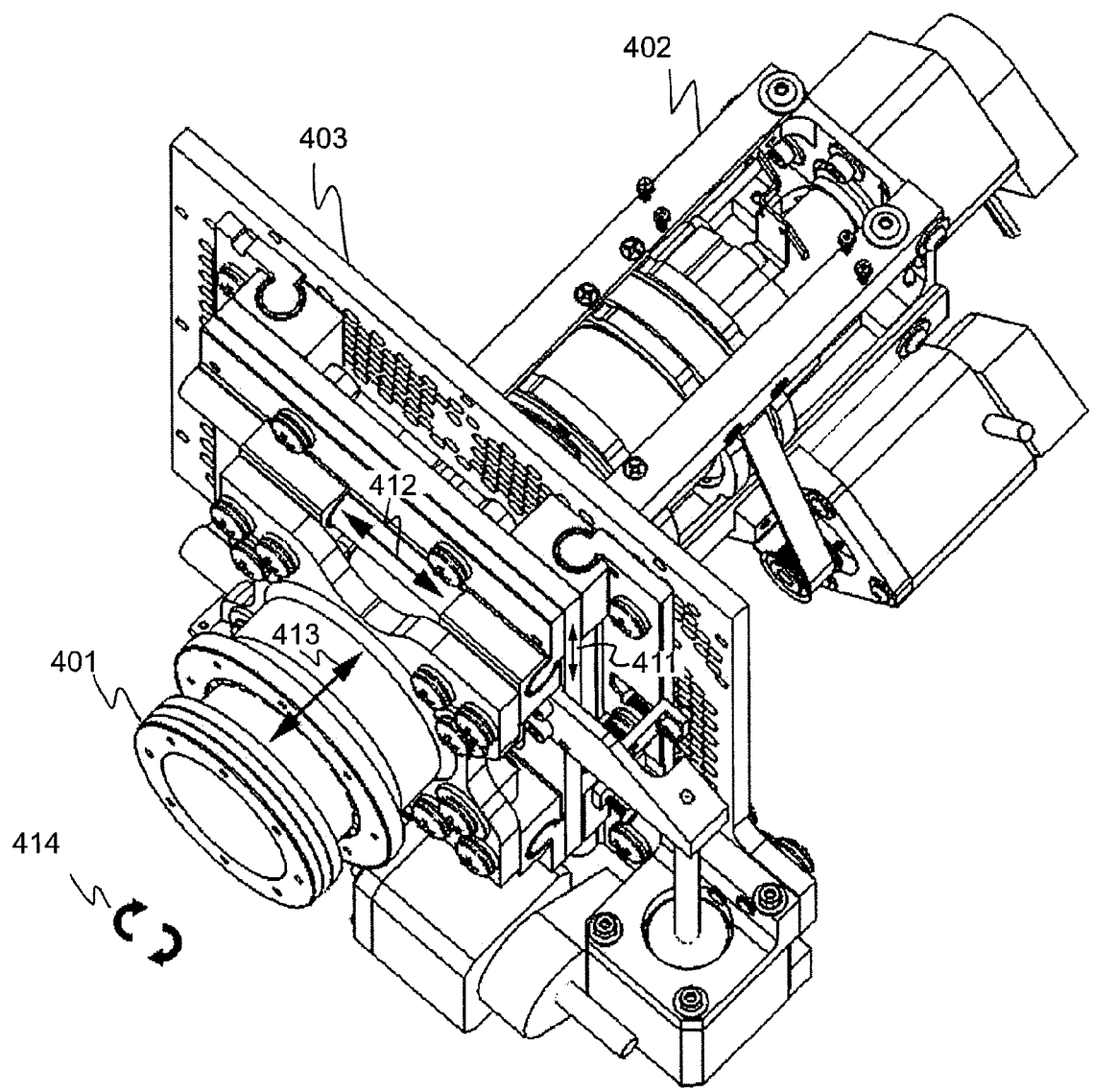
FIG. 4 illustrates an isometric view of a prior art compact arc scanning head positioning mechanism.

FIG. 4 illustrates an isometric view of a prior art compact scan head positioning mechanism. An axial carrier frame 402 and mounting plate 403 are fixed to the main arc scanner assembly. The scanner head mount arm 401 can move axially back and forth as shown by arrow 413. The scanner head mount arm 401 can rotate about its axis as shown by arrows 414. The scanner head mount arm 401 can move up and down as shown by arrows 411 and back and forth as shown by arrows 412. The scan head, which is mounted on the scanner head mount arm 401, is not shown in this figure.

Figure 5:
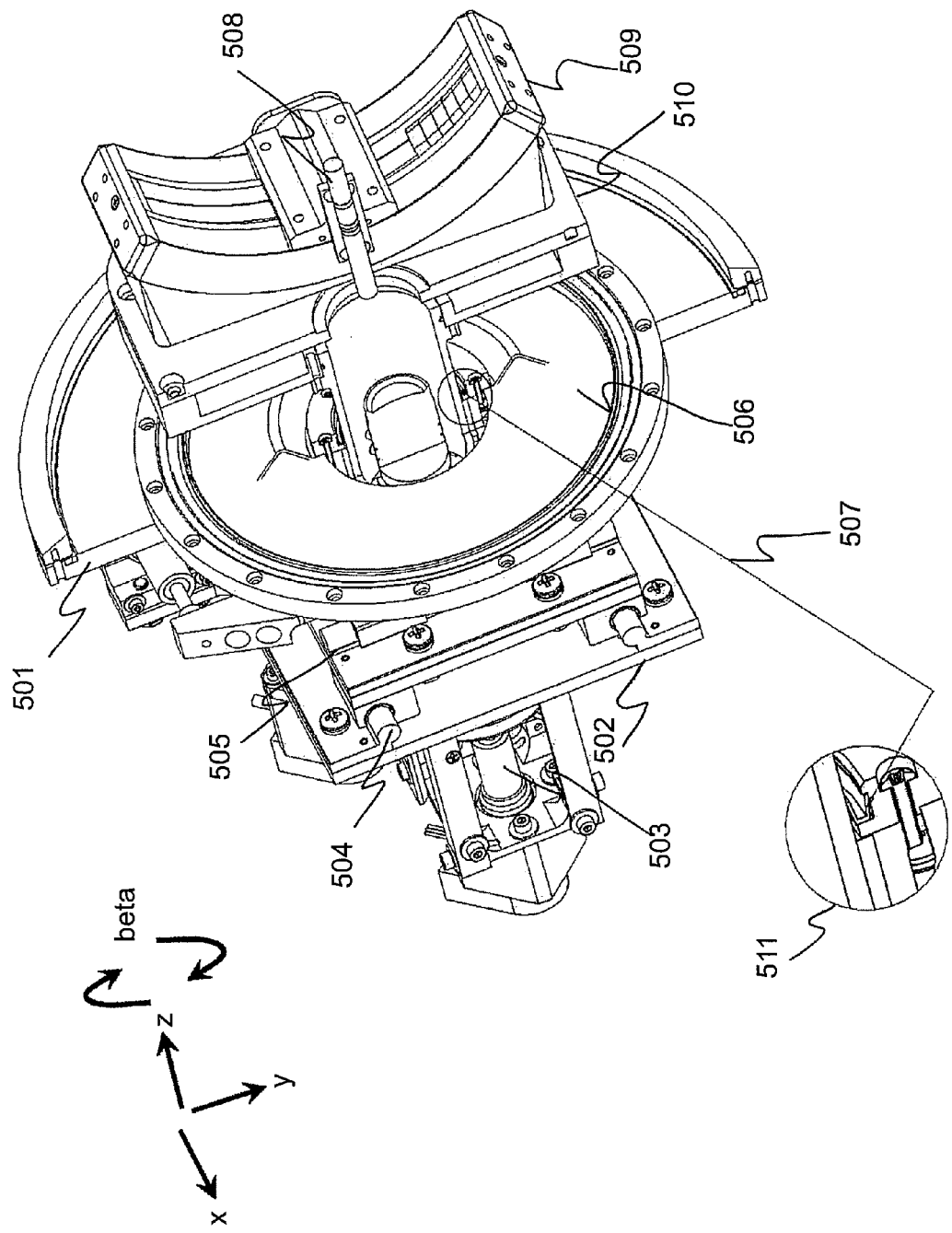
FIG. 5 further illustrates a prior art compact arc scanning head positioning mechanism.

FIG. 5 further illustrates a prior art compact scan head positioning mechanism. FIG. 5 shows an arc scanner head 509 with ultrasonic transducer 508 mounted on the end of a scanner head mount arm 510. These components (scanner head mount arm 510, scanner head 509 and ultrasonic transducer 508) are operative under water and are sealed from the rear portion of the positioning mechanism by a translational seal 506 and a rotational seal 507. The translational seal 506 is preferably formed by a large rubber membrane that can flex with the small x and y motions required by the scanning head positioner, though any sealing mechanism may be employed. The z-axis seal and rotational seal 507 are attached to a stationary plate 501 which is affixed to the main arc scanner assembly. The z-axis and rotational seal 507 is typically formed by a circumferential groove type sealing mechanism with the groove facing into the water, though any sealing mechanism may be employed. The sealing surfaces are preferably anodized aluminum. Stationary plate 502 is also affixed to the main arc scanner assembly. The scanning head can be moved back and forth axially (the z-direction) by axial piston 503 or another suitable mechanism. The scanning head can be rotated (the beta-direction) about the z-axis by a rotary stepping motor (not shown) or another suitable device. The scanning head can be moved up and down (the y-direction) by piston 505 or another suitable mechanism. The scanning head can be moved from side to side (the x-direction) by piston 504 or another suitable mechanism. The components to the left or rear of stationary plate 501 remain in ambient air while the components to the right or font of stationary plate 501 are in immersed in water when the arc scanner is operational. This same scan head positioning mechanism can be used with the rotatable transducer head of the present invention.

The carriage can be moved along the arc guide using any of a number of motive methods. In the preferred embodiment, there is a position encoder, preferably incremental and magnetic, borne by the guide track and the carriage, that allows external circuitry to sense the position of the carriage along the track. The positional information is used to control the a linear motor such as described in U.S. patent application Ser. No. 12/347,674 which moves the carriage moves along the track. It is also used to trigger the sending of ultrasonic pulses so as to provide, for example, a uniform physical spacing of the pulse-echo tracks in an ultrasound B-scan image. As can be appreciated, the positional information can be used to trigger the sending of ultrasonic pulses so as to provide a non-uniform but desired physical spacing of the pulse-echo tracks in an ultrasound B-scan image.

The magnetic positioning system provides precise position information for the transducer carriage along the arc guide assembly which, in turn, allows for a precise and accurate ultrasonic scan to be made. The scan head consists of an arc guide assembly; a transducer carriage assembly; and a magnetic encoder which is contained in a housing mounted on the side of the transducer carriage assembly. The magnetic encoder senses its position by reading a magnetic strip which is attached to the arc guide track. The operation of such a magnetic strip is described in U.S. patent application Ser. No.

12/347,674. An encoder is capable of providing 1 micron resolution or about 0.0005 degrees of angular positioning for the transducer carriage of a typical arc scanner.

Other position sensing systems are possible. These include optical systems (optical bars replace the magnetic combs), mechanical systems and electrical systems (such as a potentiometer). The magnetic sensing system is preferred over the optical system which requires periodic cleaning and the mechanical system which is subject to buildup of mineral and other deposits.

Important Dimensions for Lens Replacement

Figure 6:
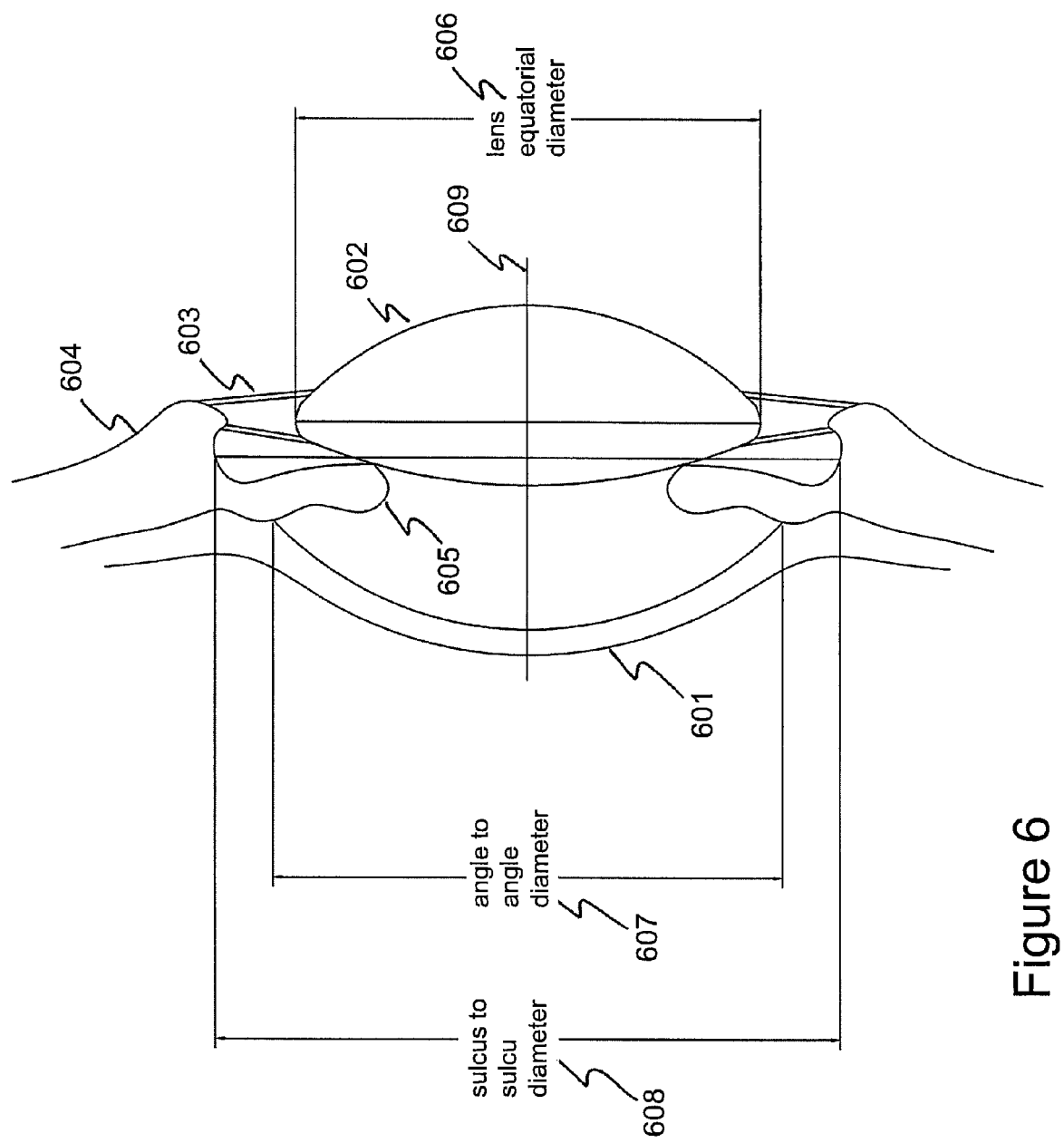
FIG. 6 is a schematic showing important dimensions for lens replacements.

FIG. 6 is a schematic showing important dimensions that can be used for lens replacements. In U.S. Pat. No. 7,048,690, several important dimensions are noted that relate to lens implantation. Some of these are illustrated in FIG. 6 which includes eye components such as the cornea 601, the lens 602, the iris 605, the ciliary body 604 and the zonules 603. The significant dimensions noted in US 7,048,690 include the angle-to-angle diameter 607, the sulcus-to-sulcus diameter 608 and the lens equatorial diameter 606. Other important dimensions include the distance from the anterior surface of the cornea to the angle-to-angle diameter along the optical axis (the angle plane depth); the distance between the anterior surface of the cornea and the sulcus-to-sulcus diameter 608 along the optical axis (the sulcus plane depth); and the thickness of the lens along the optical axis. These dimensions can be measured by current arc scanners.

In addition, it is desirable to measure the connection points of the zonules to the anterior and posterior surface of the lens and the connection points of the zonules to the ciliary body and also to image the entire lens capsule along multiple meridians. Current arc scanners cannot image the zonule attachment points and cannot image the ends of the lens capsule since they are generally not capable of emitting acoustic pulses that reflect normally from these features. The compound scanning head of the present invention is designed to image most or all of these features. This new capability will enormously improve the ability of researchers to design replacement lenses as well as assist surgeons in planning, executing and post-operative diagnoses of lens implantation procedures, whether implanting clear lenses or accommodative lenses.

Compound Scanning Head

FIG. 7 is a schematic of a compound scanning head of the present invention. FIG. 7a shows an arc guide track 701 on which is mounted a transducer carriage 703 that moves back and forth on the guide track 701 as shown by arrow 702. A transducer 704 is mounted on the carriage 703 such that the transducer is rotated (or oscillated) back and forth as shown by arrows 705. In the preferred configuration, the plane of the transducer head motion as depicted by arrows 705 is coincident with the plane of the arc guide as depicted by arrows 702. The arc guide track 701 is circular with a fixed center of curvature which, with the arc guide track 701, defines a plane. The sector head transducer is rotated back and forth in this plane and so produces acoustic pulses and records reflected acoustic pulses that are in the same plane as the arc guide track. As the carriage moves, its location is always known by means of a magnetic positioning system. This positioning system provides precise positional information for the transducer carriage and hence for the transducer along the arc guide track 701. The transducer head 704 oscillates rapidly back and forth so that it produces pulses and records reflections at several angles (for example shown in FIGS. 7b and 7c) with respect to its normal position (aligned with the axis of symmetry of the transducer housing 804) as depicted in FIG. 7a. The normal position depicted in FIG. 7a results in a pulse and a reflection along a line between the transducer head and the center of curvature of the arc track 701.

Figure 8:
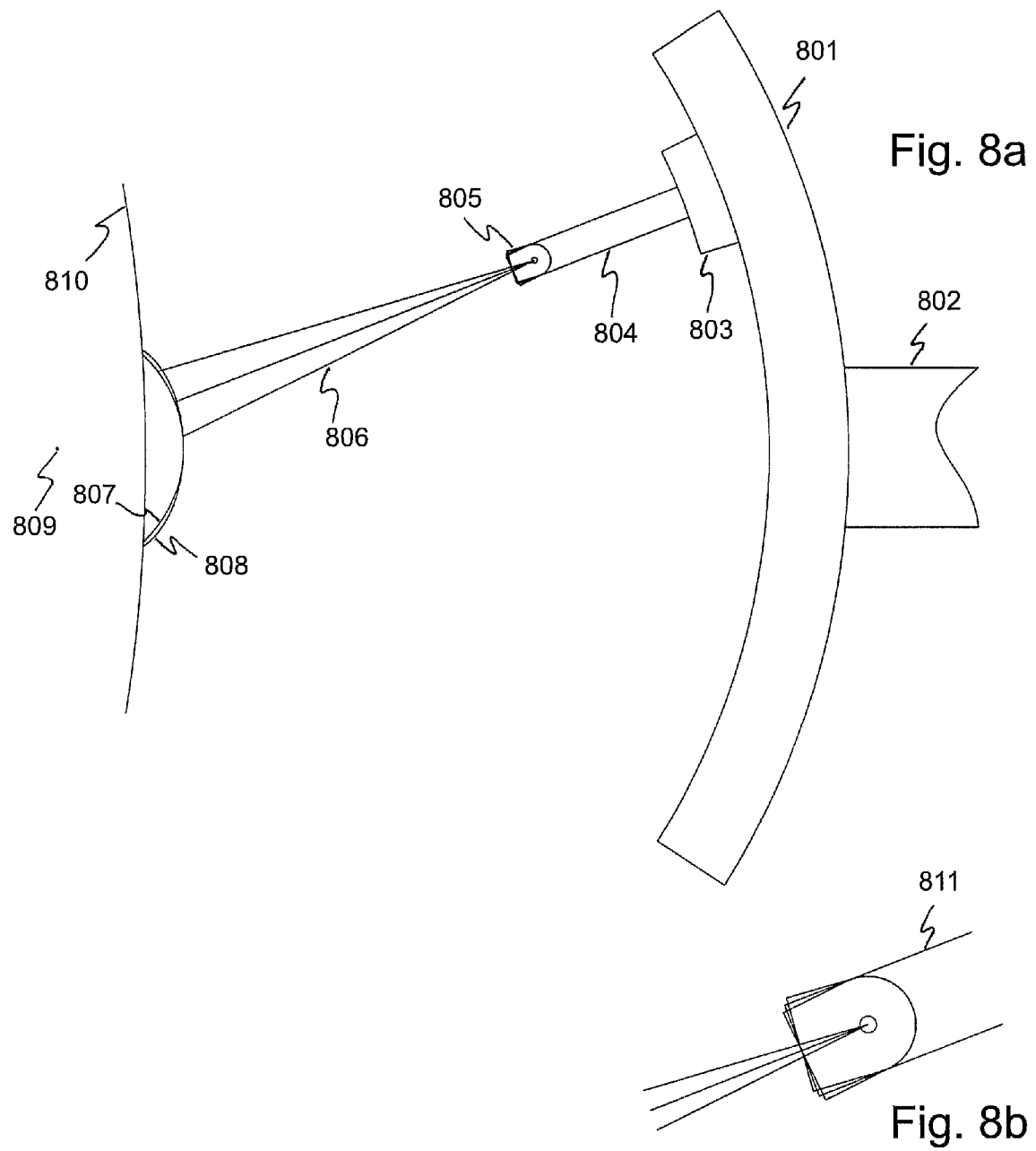
FIG. 8 is a schematic of a compound scanning head of the present invention illustrating enhanced imaging.

FIG. 8 is a schematic of a compound scanning head of the present invention illustrating enhanced imaging. An arc guide track 801 is shown mounted on a scan head positioning mechanism 802. An example of a scan head positioning mechanism is described previously in FIGS. 4 and 5. The scan head positioner 802 orients the arc guide track 801 such that the center of curvature 809 of the arc guide track 801 is (1) approximately coincident with the center of curvature of an eye surface of interest (in this example, the surface of interest may be a specular surface 807 on or within the cornea); and (2) such that the plane formed by the arc track 801 and its center of curvature 809 is parallel to a section of interest within an eye component being scanned (in this example, the section of interest may be a desired section through a cornea). The section of interest is also called a meridian. A transducer housing 804 is shown mounted rigidly on a transducer carriage 803. A rotatable transducer head 805 is shown mounted on the transducer housing 804. In this figure, the transducer head is shown, for example, in three of many possible positions: normal (aligned with the axis of symmetry of the transducer housing 804), 5 degrees above normal (but still in the plane of the arc track) and 5 degrees below normal (but still in the plane of the arc track). In each position, a transmitted pulse follows a path such as indicated by rays 806. In the normal position, the projected ray passes through the center of curvature 809. In any off-normal position, the projected ray would pass slightly above or below the center of curvature 809.

The surface 807 or 808 of an eye component (such as, for example, the anterior surface of a cornea, the anterior surface of a natural lens or an incision within a cornea) is shown along with a sealing surface 810 which maintains the surface of the eye in a water bath such as described in U.S. patent application Ser. No. 12/347,674. Surface 808 is circular and has a constant radius of curvature with its center of curvature approximately at the location of the center of curvature 809 of the arc guide track 801 and transducer head 805 when the transducer head 805 is in normal position. Surface 807 is slightly elliptical.

In the case of surface 808 with its center of curvature always approximately at the location of the center of curvature 809 of the arc guide track 801 and transducer head 805, the transmitted pulse will be always be reflected back along its transmission path and a strong received pulse will be captured by the transducer head 805 when in its normal position (aligned with the axis of symmetry of transducer housing 804). When the transducer head 805 is not in its normal position (ie it has moved to an angle above or below its normal position), the strength of the received pulse captured by the transducer head 805 will be diminished, diminishing rapidly as the angle increases away from its normal position.

In the case of slightly elliptical surface 807 with its variable center of curvature, the transmitted pulse will only be reflected back along its transmission path and a strong received pulse captured by the transducer head 805, when the transducer head rotates into a position where the transmitted pulse reflects normally from the surface 807. When the transducer head 805 is at any other angle, the strength of the received pulse captured by the transducer head 805 will be diminished, diminishing rapidly as the angle increases away from the angle at which the transmitted pulse reflects normally from the surface 807.

Thus, for any eye component surface that is not perfectly circular with approximately the same center of curvature as the arc guide track, the compound, rotatable head will almost always produce a stronger received pulse than a fixed head with its transducer aligned with the axis of symmetry of the transducer housing.

FIG. 8 also includes a close-up 811 of the rotatable transducer head 805 with the transducer head in three possible positions: normal (aligned with the axis of symmetry of the transducer housing 804), 5 degrees above normal and 5 degrees below normal. As can be appreciated, the rotatable head can be moved through very small angular displacements between pulses and can be rotated through a total included angle of up to about 60 degrees if desired. Thus it is possible to emit pulses with very small angular increments over a very large total angular range.

Figure 9:
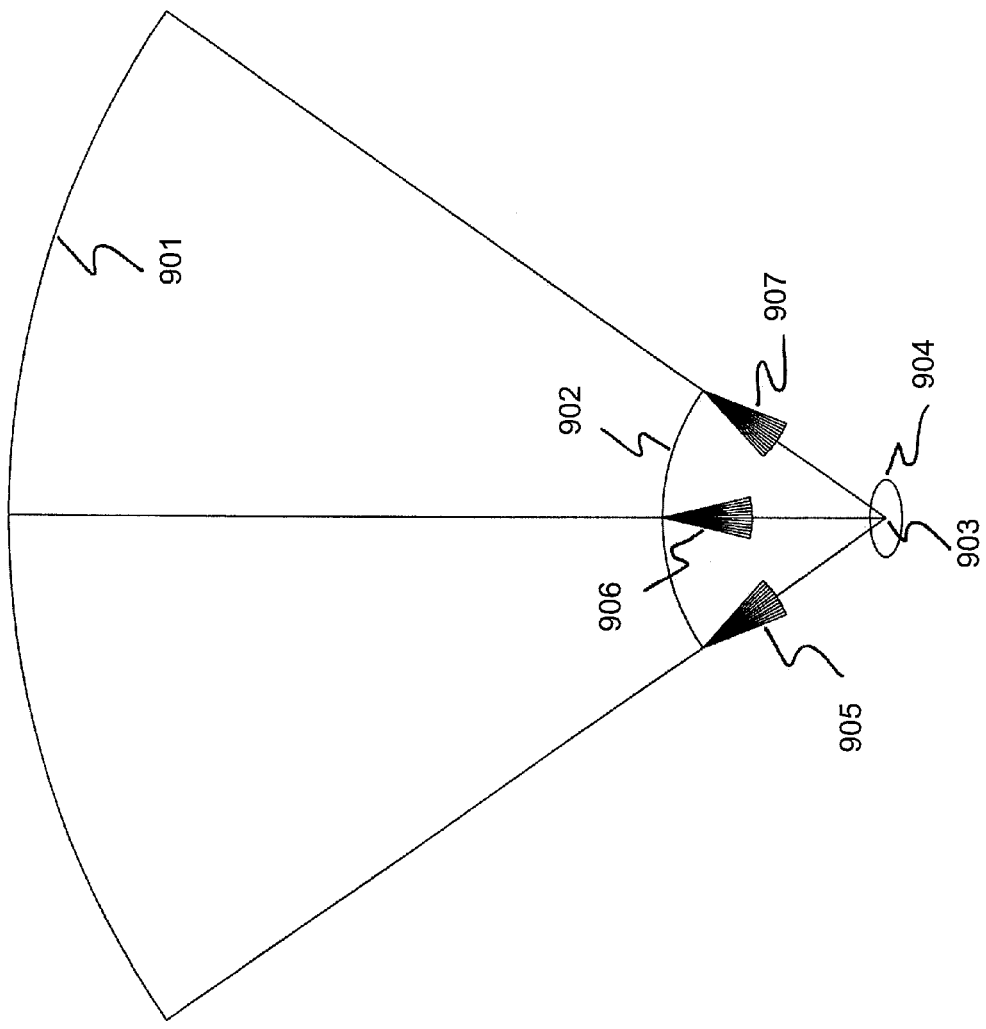
FIG. 9 is a schematic of a compound scanning setup.

FIG. 9 is a schematic of a compound scanning setup. This figure shows a typical arc guide track 901 and the corresponding arc path of the transducer head 902. The radius of curvature of the arc guide track 901 is typically in the range of 100 millimeters ±20 millimeters and the radius of curvature of the arc path of the transducer head is typically in the range of 15 to 50 millimeters. The center of curvature of the arc guide track 901 and transducer head path 902 is shown coinciding with the center 903 of a lens 904. The curvature of the arc guide track is designed to approximate the curvature of the anterior surface of the cornea and/or lens (the anterior surface being the surface closest to the transducer head. The range of included angles 905 is shown for a sector scan head or compound head positioned at the far left of the transducer head arc path 902. The range of included angles 906 is shown for a sector scan head or compound head positioned at the mid point of the transducer head arc path 902. The range of included angles 907 is shown for a sector scan head or compound head positioned at the far right of the transducer head arc path 902. The range of included angles for a sector scan head or compound head is typically in the approximate range of about ±5 to about ±25 degrees from its "zero" position (aligned with the axis of symmetry of the transducer housing). The range of included angles for rotating a transducer of the present invention may be in the approximate range of about ±5 to about ±45 degrees from its "zero" position. As will be shown in FIGS. 10 and 11, the range of scan angles that can be utilized by such a compound scan head as it traverses the arc is much greater than a fixed arc scan head. As a result, the compound scan head can always emit acoustic pulses that reflect nearly normally to almost the entire anterior and posterior surfaces of a lens and its connecting parts such as the zonules and therefore an essentially complete acoustic image of a lens (whether a natural lens or artificial lens) can be generated.

Figure 10:
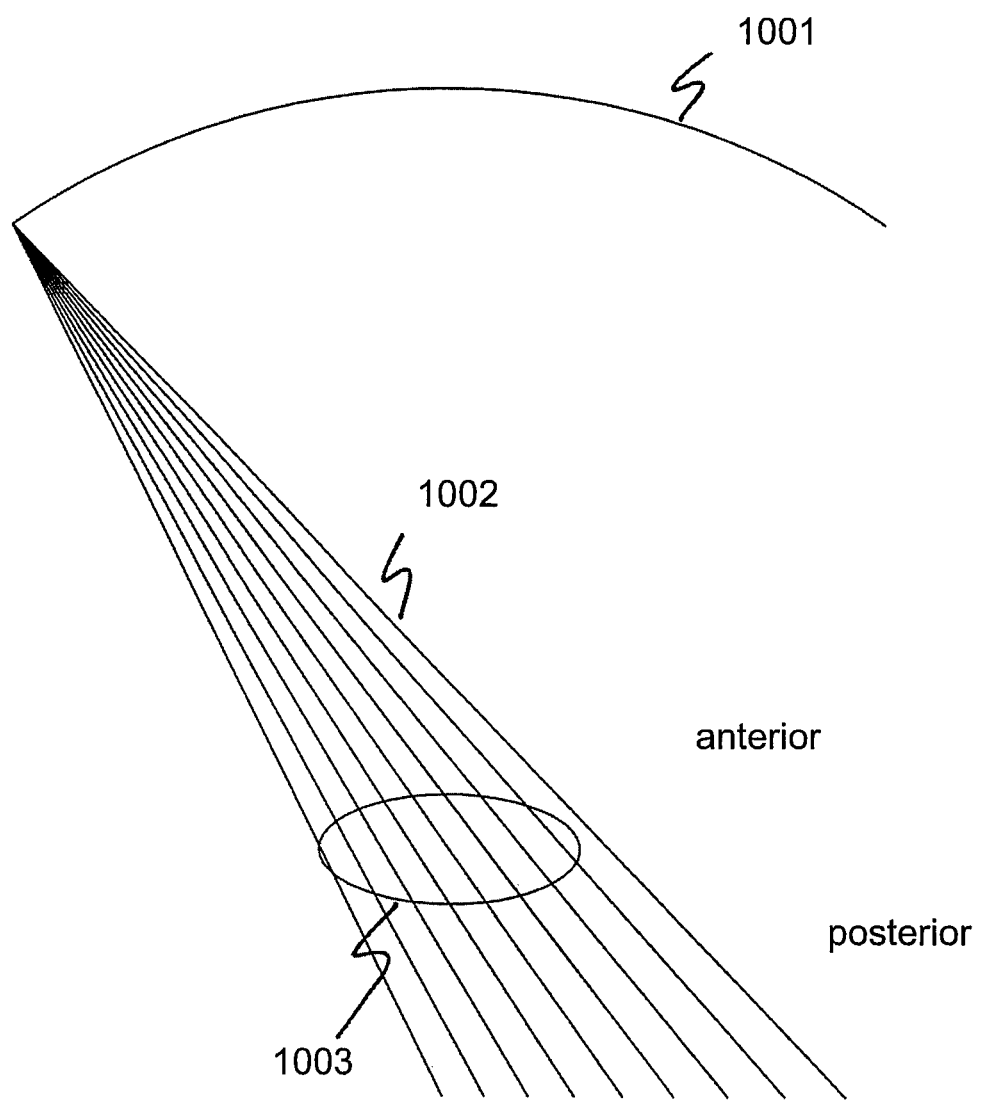
FIG. 10 is a schematic of a sector scan coverage from the left side of an arc.

FIG. 10 is a schematic of a typical sector scan coverage from the left side of an arc. A number of representative rays 1002 (emitted acoustic pulses) are shown for a compound head positioned at the far left of the transducer head arc path 1001. The rays 1002 are shown intersecting the anterior and posterior surfaces of a lens 1003. As can be seen, some of the rays intercept the surface at nearly right angles on the left side anterior and right side posterior surfaces of the lens.

Figure 11:
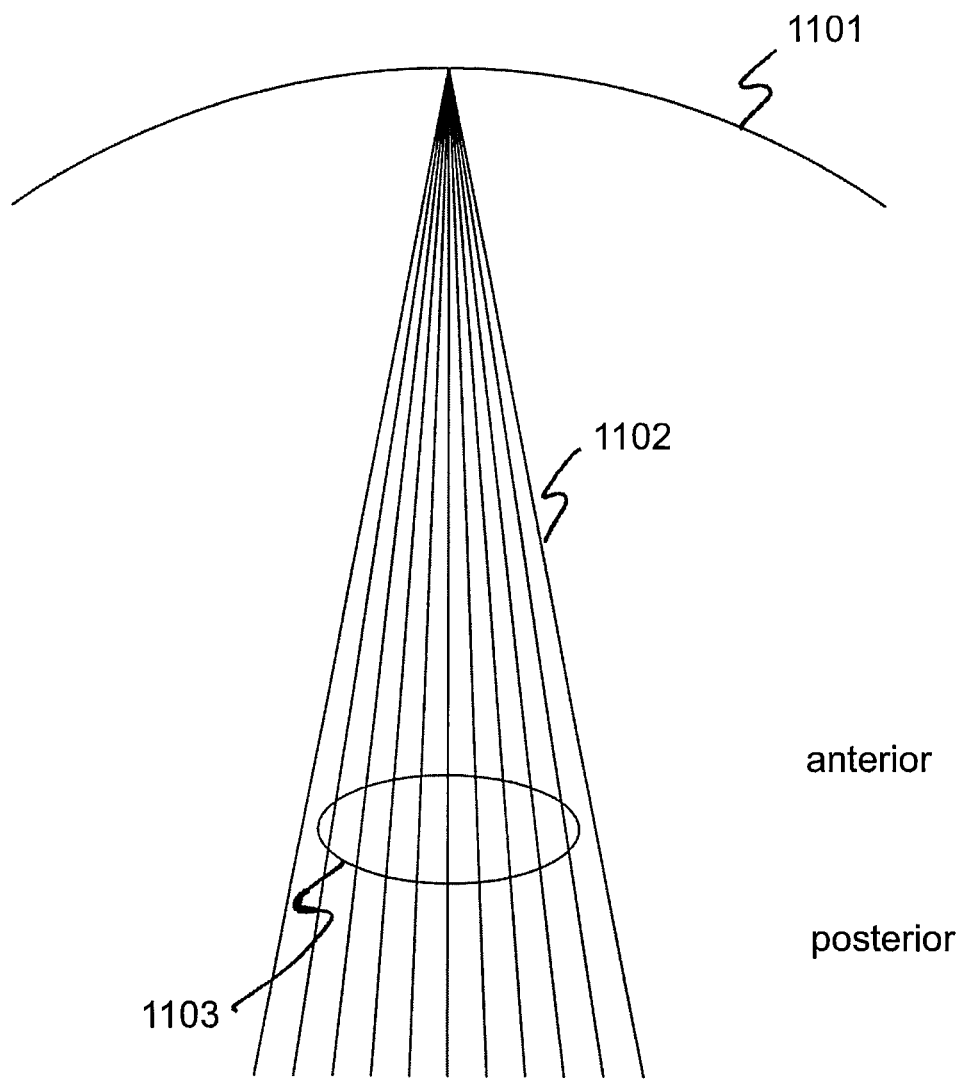
FIG. 11 is a schematic of a sector scan coverage from the center of an arc.

FIG. 11 is a schematic of a typical sector scan coverage from the center of an arc. A number of representative rays 1102 (emitted acoustic pulses) are shown for a compound head positioned at the mid point of the transducer head arc path 1101. The rays 1102 are shown intersecting the anterior and posterior surfaces of a lens 1103. As can be seen, some of the rays intercept the surface at nearly right angles on segments of both the anterior and posterior surfaces of the lens near the apex of these surfaces.

As can be appreciated, intermediate positions of the compound head will produce normal or near normal reflections at intermediate locations on the anterior and posterior lens surfaces. In this way, an arc scanner with a sector scanning head can produce a strong acoustic image (resulting from near normal reflection) of essentially the entire anterior and posterior surface of a lens.

FIG. 12 shows a sequence of scans with a compound scanner head where the transducer is focused approximately in the center of the lens when in the position shown in FIG. 12b. In this example, the radius of curvature of the arc guide track is 100 millimeters; the transducer diameter is 5 mm; the 50 MHz transducer focal length is 13 mm; and the included angle of the arc guide track is 70 degrees. These are typical dimensions for arc scanners that have been available commercially. This sequence illustrates the range of acoustic pulse vectors that a compound head scanner can achieve. FIG. 12a shows an arc guide track 1201 whose center of curvature is at point 1206. The main transducer body 1202 is shown positioned in the middle of the arc guide track which is roughly aligned with an eye 1205. In this example, the main transducer body is positioned at the center of the arc guide track at a reference angle of 0 degrees along the arc guide track, and a rotatable transducer head is shown rotated upwards at an angle of 10 degrees relative to the axis of the transducer body 1202. The angular limits of the arc guide track 1204 are typically about ±35 degrees where 0 degrees is the reference center of the arc guide track 1201. FIG. 12b shows the main transducer body aligned at 0 degrees along the arc guide track and the rotatable transducer head is now aligned with the axis of the transducer body. FIG. 12c shows the main transducer body aligned at 0 degrees along the arc guide track and the rotatable transducer head is shown rotated downwards at an angle of minus 10 degrees relative to the axis of the transducer body. FIG. 12d shows the main transducer body moved along the arc guide track to an angle of 25 degrees above the center reference position shown in FIG. 12b. The rotatable transducer head shown rotated upwards at an angle of 10 degrees relative to the axis of the transducer body. FIG. 12e shows the main transducer body at an angle of 25 degrees above the center reference position along the arc guide track and the rotatable transducer head is now aligned with the axis of the transducer body. FIG. 12f shows the main transducer body at an angle of 25 degrees above the center reference position along the arc guide track and the rotatable transducer head is shown rotated downwards at an angle of minus 10 degrees relative to the axis of the transducer body. Each of these positions is discussed in further detail in FIGS. 13 through 17 with emphasis on which components of the eye can be imaged. With the combined motion of the transducer carriage along the arc guide track (±35 degrees) and the full angle of rotation of the transducer head (±25 degrees), the acoustic ray vectors can cover an included angle of (±60 degrees).

Figure 13:
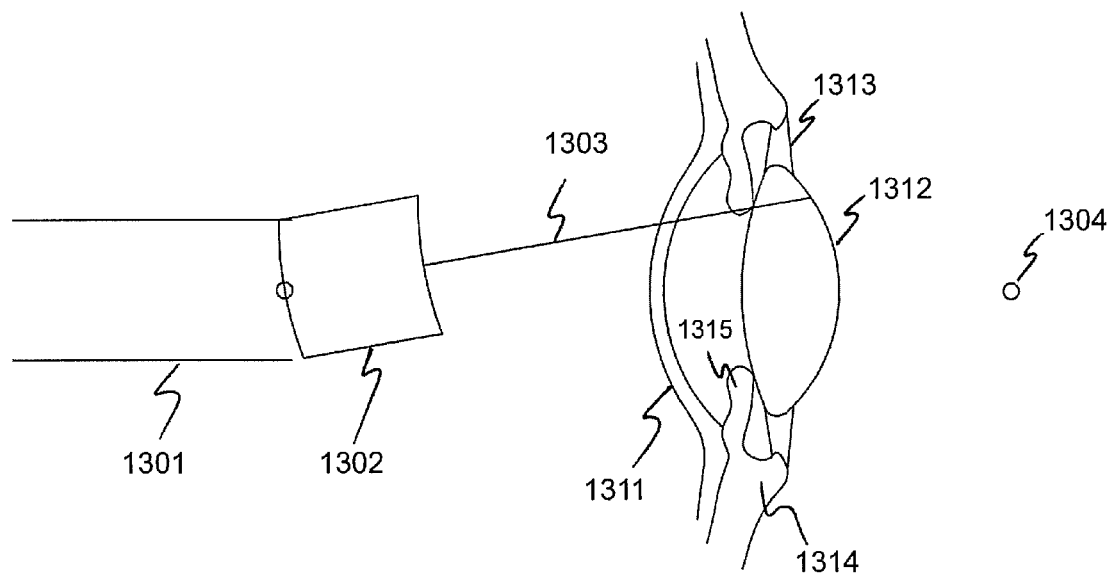

FIG. 13 shows an up close schematic of FIG. 12a. The main transducer body 1301 is shown positioned in the middle of the arc guide track aligned at a reference angle of 0 degrees along the arc guide track. The rotatable transducer head 1302 is shown rotated upwards at an angle of 10 degrees relative to the axis of the transducer body 1301. The path or vector 1303 of an acoustic pulse emitted by the transducer is shown relative to the cornea 1311 and the lens 1312. Other components of the eye include the iris 1315, the ciliary body 1314 and the zonules 1313. As can be seen, vector 1303 is not normal to any of the cornea or lens surfaces but may be perpendicular to other components of interest such as the surfaces of the ciliary body, the zonules or the iris. In this example, the transducer is approximately focused along the line connecting the anterior and posterior surfaces of lens capsule 1312. The center of curvature 1304 of the arc guide track is shown for reference.

Figure 14:
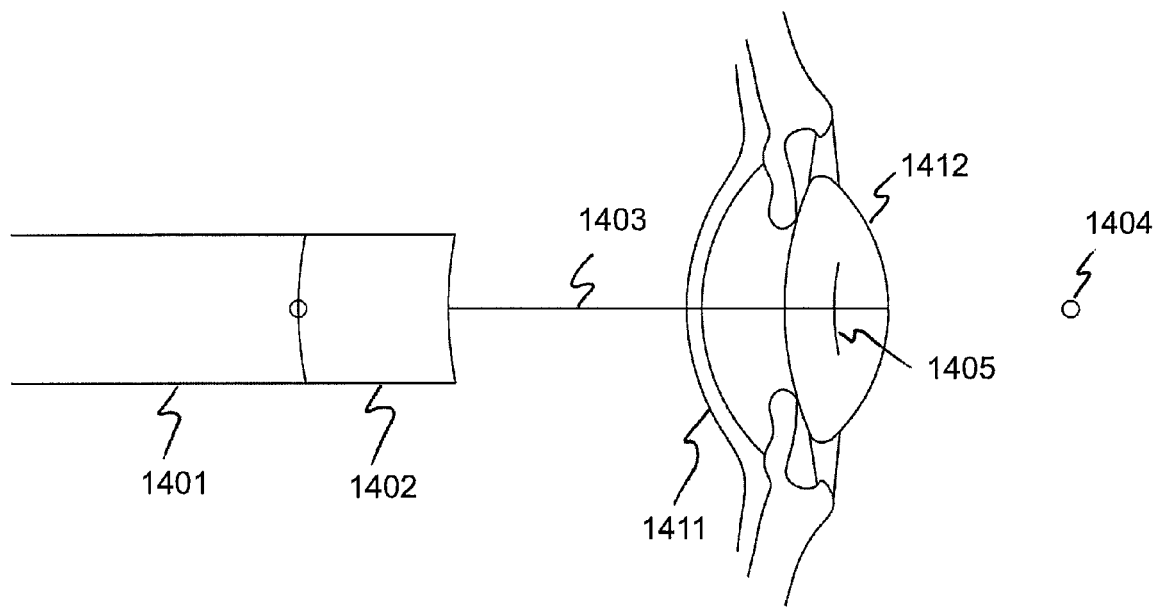
FIG. 14 shows an up close schematic of FIG. 12b.

FIG. 12c is the mirror image of FIG. 12a FIG. 14 shows an up close schematic of FIG. 12b. The main transducer body 1401 is shown positioned in the middle of the arc guide track aligned with the main transducer body at a reference angle of 0 degrees along the arc guide track. The rotatable transducer head 1402 is shown aligned with the axis of the main transducer body 1401 at an angle of 0 degrees relative to the axis of the transducer body 1401. The path or vector 1403 of an acoustic pulse emitted by the transducer is shown relative to the cornea 1411 and the lens 1412. In this example, the transducer is approximately focused along the line connecting the anterior and posterior surfaces of lens capsule 1412. The approximate depth of focus 1405 of the transducer is shown as being approximately in the middle of the lens capsule 1412. As can be seen, vector 1403 is normal to the cornea surfaces and the anterior lens surface. The center of curvature 1404 of the arc guide track is shown for reference.

Figure 15:
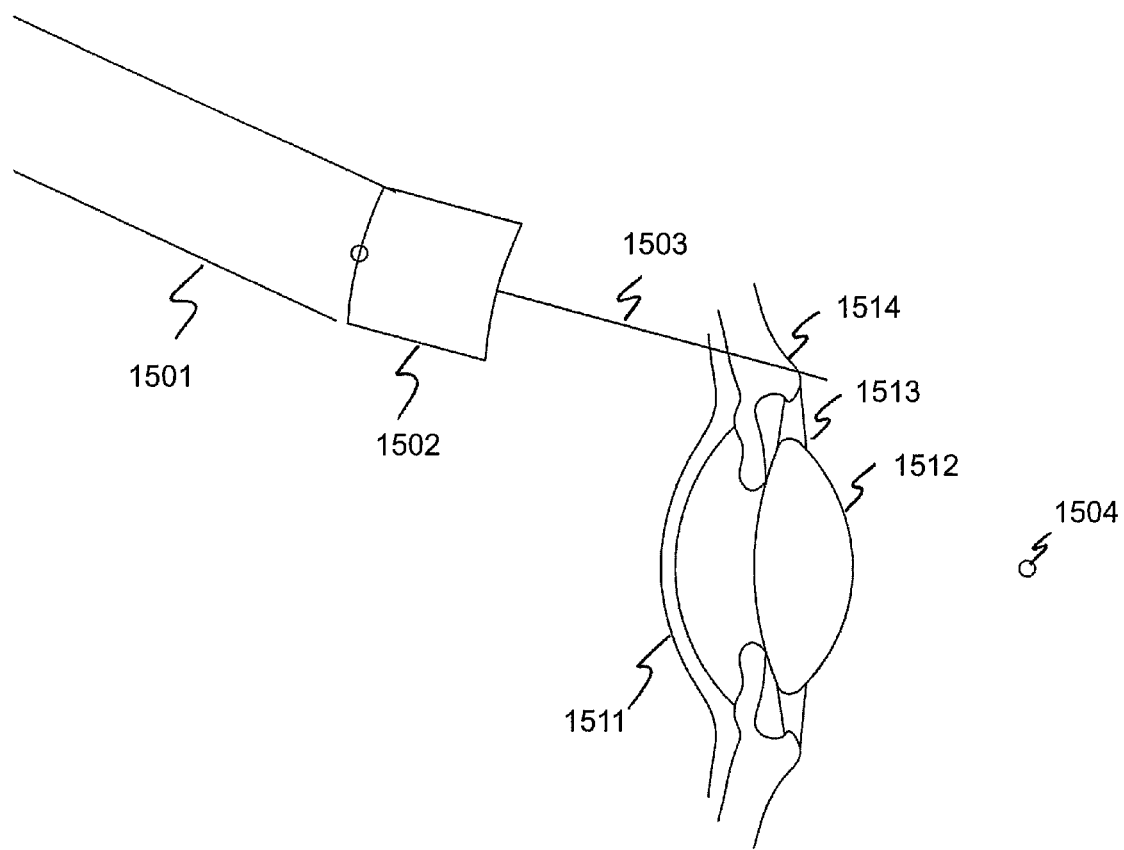
FIG. 15 shows an up close schematic of FIG. 12d.

FIG. 15 shows an up close schematic of FIG. 12d. The main transducer body 1501 is shown positioned at an angle of 25 degrees along the arc guide track. The rotatable transducer head 1502 is shown rotated upwards at an angle of 10 degrees relative to the axis of the transducer body 1501. The path or vector 1503 of an acoustic pulse emitted by the transducer is shown relative to the cornea 1511 and the lens 1512. Other components of the eye include the ciliary body 1514 and the zonules 1513. As can be seen, vector 1503 may be perpendicular to other components of interest such as the surfaces of the ciliary body 1514 and the zonules 1513 and is approximately normal to the ciliary body where the posterior zonules attach. In this example, the transducer is approximately focused along the line connecting the anterior and posterior surfaces of lens capsule 1512. The center of curvature 1504 of the arc guide track is shown for reference.

Figure 16:
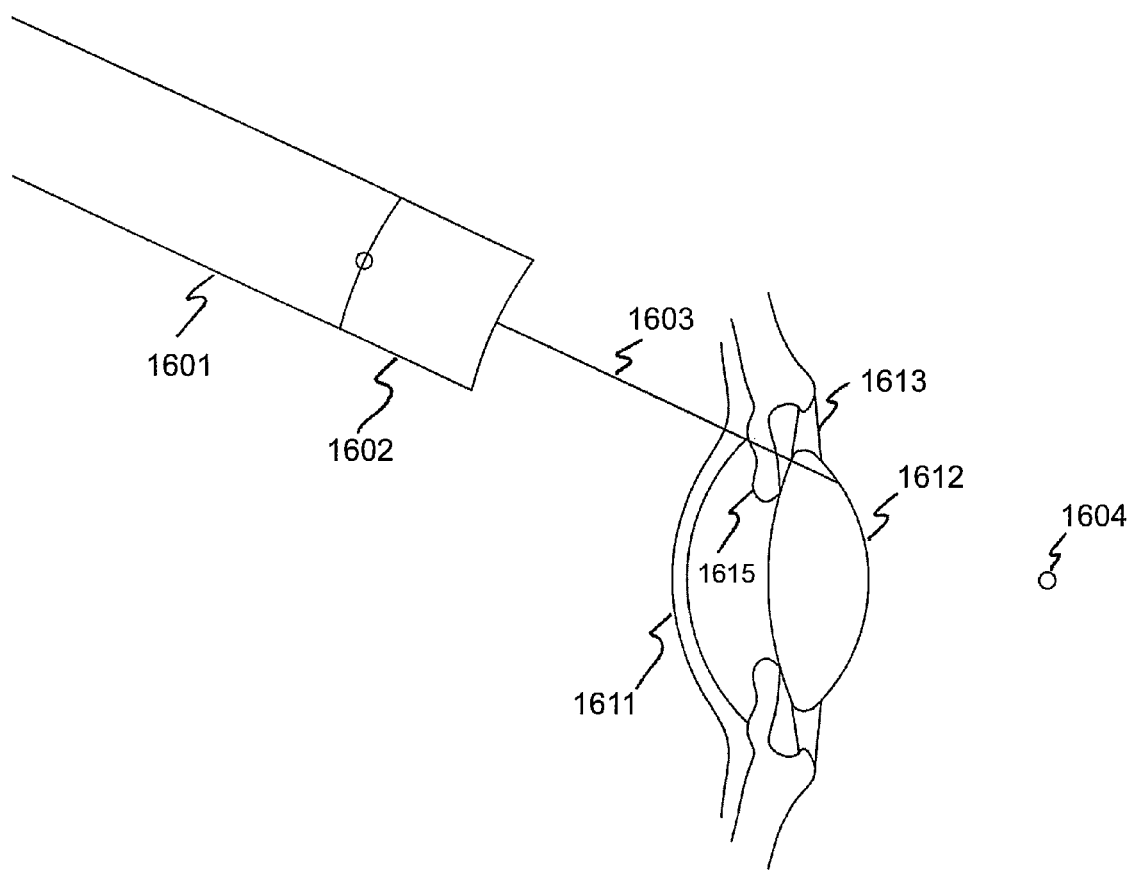
FIG. 16 shows an up close schematic of FIG. 12e.

FIG. 16 shows an up close schematic of FIG. 12e. The main transducer body 1601 is shown positioned at an angle of 25 degrees along the arc guide track. The rotatable transducer head 1602 is shown aligned with the transducer body 1601 at an angle of 0 degrees relative to the axis of the transducer body 1601. The path or vector 1603 of acoustic pulses emitted by the transducer is shown relative to the cornea 1611 and the lens 1612. Other components of the eye include the iris 1615 and the zonules 1613. As can be seen, the vector 1603 may be perpendicular to other components of interest such as the iris 1615, the zonules 1613 and is approximately normal to the anterior surface of the lens capsule. In this example, the transducer is approximately focused along the line connecting the anterior and posterior surfaces of lens capsule 1612. The center of curvature of the arc guide track 1604 is shown for reference.

Figure 17:
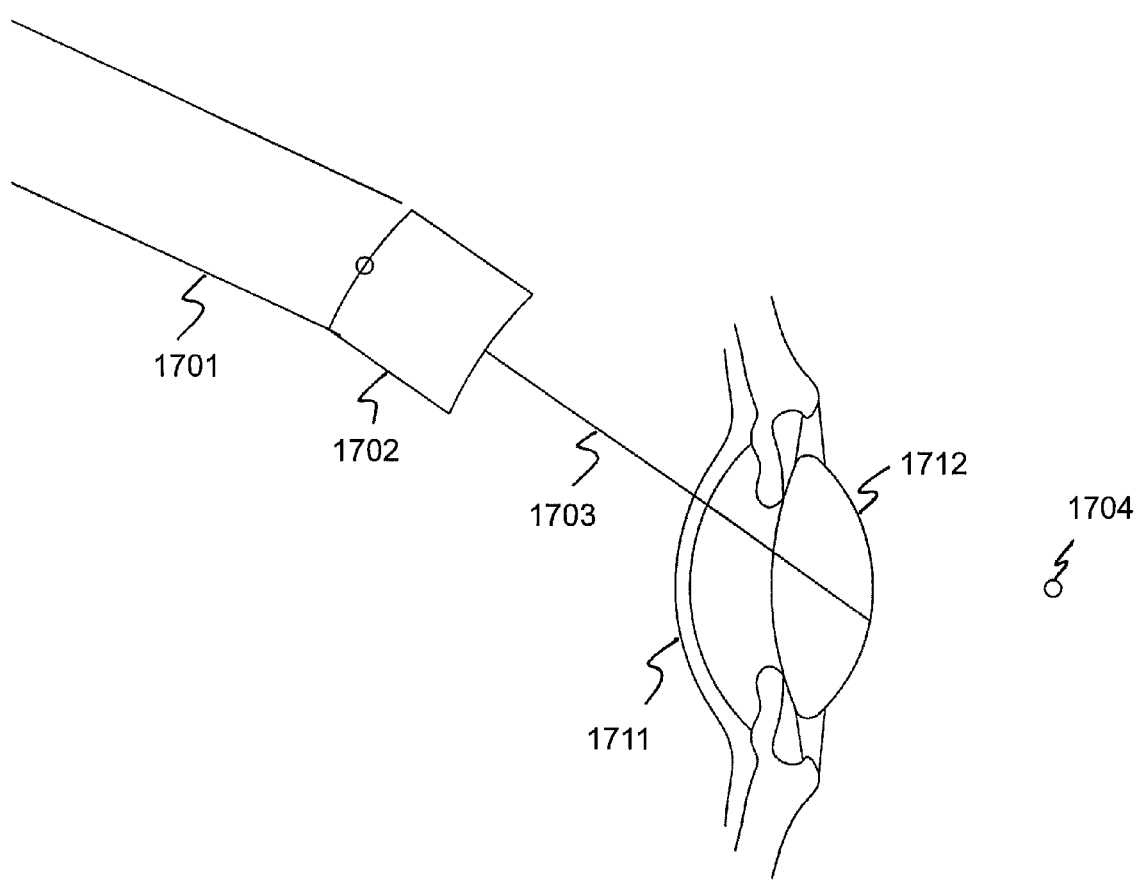
FIG. 17 shows an up close schematic of FIG. 12f.

FIG. 17 shows an up close schematic of FIG. 12f. The main transducer body 1701 is shown positioned at an angle of 25 degrees along the arc guide track. The rotatable transducer head 1702 is shown rotated downwards at an angle of minus 10 degrees relative to the axis of the transducer body 1701. The path or vector 1703 of an acoustic pulse emitted by the transducer is shown relative to the cornea 1711 and the lens 1712. As can be seen, vector 1703 is not perpendicular to any major eye features although this acoustic pulse may detect surfaces of foreign objects within the eye. In this example, the transducer is approximately focused along the line connecting the anterior and posterior surfaces of lens capsule 1712. The center of curvature 1704 of the arc guide track is shown for reference.

The above example shows how a rotatable compound head can oscillate back and forth at every arc scan carriage position and find at least one transmission path that impinges normally or very close to normally on any local specular or non-specular surface of interest, even when the local surface has a center of curvature not coincident withe the center of curvature of the arc guide track or when the local surface is uneven on a scale close to the resolution of the acoustic scanning system.

Typically the arc carriage moves along the arc guide track at speeds from 0 to about 2 meters per second. The compound scan head is moved back and forth through an angle of about 5 to about 15 degrees above and below its normal position (aligned with the axis of symmetry of the transducer housing) and in a plane defined by the arc guide track and its center of curvature. The compound scan head can be oscillated back and forth at a frequency in the range of about 500 to about 2,000 Hz. The transducer is pulsed about 8 to about 64 times per cycle of transducer oscillation. Thus the transducer can produce many sector scan cycles (a transmitted pulse followed by a recording period for a reflected pulse) while the arc carriage moves a small fraction of its total travel along the arc guide track.

The scan head positioner orients the arc track such that the center of curvature of the arc track 801 is (1) approximately coincident with the center of curvature of an eye surface of interest; and (2) such that the plane formed by the arc track and its center of curvature is aligned with a section of interest within an eye component being scanned. As the carriage moves along the arc guide track, its location is always known by means of a magnetic or other positioning system. This positioning system is designed to provide precise positional information for the transducer carriage and hence for the transducer at any time. In addition, using electronically timed control pulses, the angle of the transducer head with respect to its normal position (aligned with the axis of symmetry of the transducer housing) is known at all times, as is the timing of each transmitted pulse. Thus every time a transmitted pulse is emitted, the exact position of the transducer head relative to a known reference is always known with precision. Thus the timing of every reflected pulse captured by the transducer can be correlated with the eye surface of interest.

Figure 18:
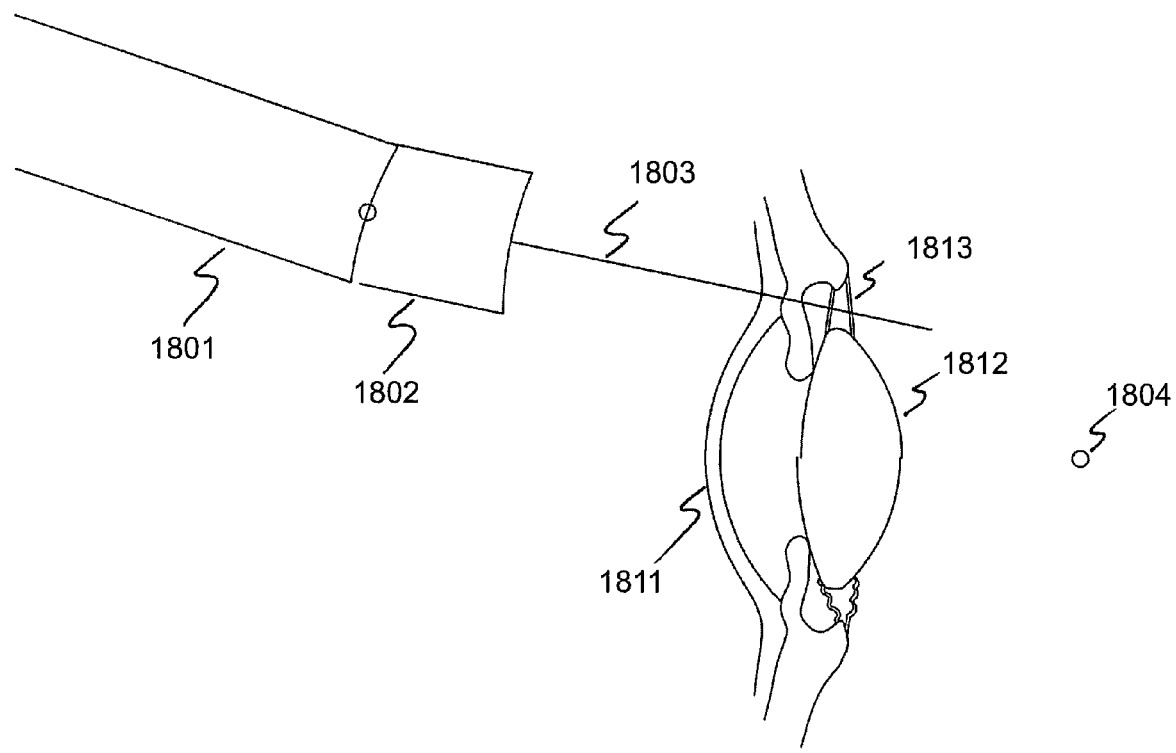
FIG. 18 is a schematic of imaging of tensioned zonules.

FIG. 18 is a schematic of imaging of tensioned zonules. This figure shows eye features including the cornea 1811, the lens 1812 and the zonules 1813. The center of curvature of the arc guide track 1804 is shown for reference. In this example, the transducer body 1801 is at an angle of 18.98 degrees above the reference angle while the angle of the acoustic vector 1803 emitted from transducer head 1802 is at an angle of 11.63 degrees above the reference angle. Thus the transducer head 1802 has rotated 7.35 degrees upward from its axial alignment position on transducer body 1801. As described previously, the 0 degree reference angle is formed by the line connecting the center of the arc track guide to the center of curvature of the arc track guide (see FIG. 13b). Acoustic pulse vector 1803 thus impinges approximately normally on zonules 1813 and should produce a strong reflected pulse from the zonules as it sweeps through additional angles around the vector trajectory shown. As can bee seen, the acoustic pulse vector will also impinge approximately normally on the anterior and posterior lens surfaces near the ends of the lens capsule as the transducer head sweeps through all of its angular positions.

Figure 19:
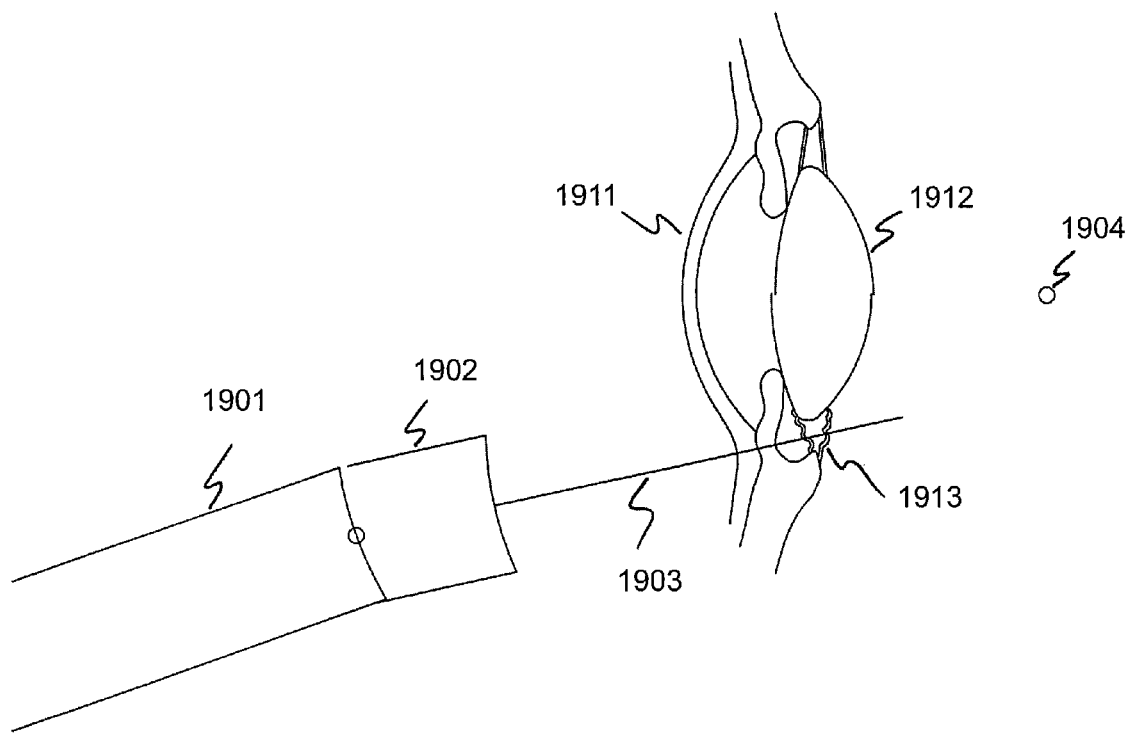
FIG. 19 is a schematic of imaging of relaxed zonules.

FIG. 19 is a schematic of imaging of zonules in which tension has been reduced on the zonules. This figure shows eye features including the cornea 1911, the lens 1912 and the zonules 1913. The center of curvature of the arc guide 1904 is shown for reference. In this example, the transducer body 1901 is at an angle of minus 19.46 degrees below the reference angle while the angle of the acoustic vector 1903 emitted from transducer head 1902 is at an angle of minus 12.48 degrees below the reference angle. Thus the transducer head

1902 has rotated minus 6.98 degrees downward from its axial alignment position on transducer body 1901. Acoustic pulse vector 1903 thus impinges approximately normally on some points on the relaxed zonules 1913 and should produce a strong reflected pulse from most of the points on the zonules as it sweeps through additional angles around the vector trajectory shown. As can bee seen, the acoustic pulse vector will also impinge approximately normally on the anterior and posterior lens surfaces near the ends of the lens capsule as the transducer head sweeps through all of its angular positions.

Modes of Operation

There are several ways in which an arc scanner apparatus can utilize a sector scanning transducer head. For example, the following describes four such modes of operation:

Mode 1—A sector scanner is mounted on the scanner positioning head only. In this configuration, a sector scanner is mounted on a positioning head such as shown in FIGS. 3 and 4. The positioning head is used to locate the sector scanner head with accuracy and precision in a known location from which a sector scan can be made. This mode has the advantage of simplicity and can make use of existing sector scanner software, or can combine existing sector scanner software with data from the positioning head to provide quantitative measurements.

Mode 2—A sector scanner is mounted on an arc carriage which is, in turn, attached to a scanner positioning head. The positioning head and arc carriage are used to locate the sector scanner head with accuracy and precision in a known location from which a sector scan can be made. This mode has the advantage of more flexibility in locating the sector head transducer while retaining much of the simplicity described in Mode 1. That is, it can make use of existing sector scanner software, or can combine existing sector scanner software with data from the positioning head to provide quantitative measurements. This mode also has the advantage that the sector scanner transducer head, when aligned with the axis of symmetry of the transducer housing can be operated as a fixed transducer head as a conventional arc scanner. Alternately, the apparatus can be operated a sector scanner from any position along the arc. In this latter case, the transducer head, when in its "zero" position, is positioned on an arc that has approximately the same center of curvature as the cornea or front surface of the lens. The "zero" position as used herein refers to the orientation of the transducer head when aligned with the axis of symmetry of the transducer housing such as shown in FIG. 13*b*.

Mode 3—In this mode, when a scan is initiated, the arc carriage is moved to a location and stopped. A sector scan is then performed. The arc carriage is then moved to a next position along the arc track, stopped and another sector scan performed. In this mode, the number of positions for which sector scans are made along the arc track can be changed independently of the rate and number of scan angles at which the sector scanner is operated. Also at each location along the arc track, the "zero" position sector scan can be used to construct a purely arc scan image.

Mode 4—In this mode, the arc carriage is moved continuously and a sector scan is made at selected intervals along the arc track. As the carriage moves along the arc track, its location is always known by means of a magnetic or other positioning system. This positioning system is designed to provide precise positional information for the transducer carriage and hence for the transducer at any time. In addition, using electronically timed control pulses, the angle of the transducer head with respect to its normal or "zero" position (aligned with the axis of symmetry of the transducer housing) is known at all times, as is the timing of each transmitted pulse. Thus, every time a transmitted pulse is emitted, the exact position of the transducer head relative to a known reference is always known with precision and accuracy. Thus, the timing of every reflected pulse captured by the transducer can be correlated with the eye surface of interest. There are at least two methods to form an image of the eye surface of interest. In the first method, the maximum strength signal from each sector scan cycle can be selected to define a point on the eye surface of interest. In the second method, all the reflected signals from each sector scan cycle can be added (with appropriate correction for any change in position) to define a point on the eye surface of interest.

In many instances, it is desired to do a sector scan in the same plane as the arc track. However, it may be desirable to do a sector scan at various angles with respect to the plane of the arc track, including at an angle orthogonal to the plane of the arc track. As described previously, the carriage location along the arc track is always known by means of a magnetic or other positioning system. This positioning system is designed to provide precise and accurate positional information for the transducer carriage and hence for the transducer at any time. In addition, using electronically timed control pulses, the angle of the transducer head with respect to its normal or "zero" position (aligned with the axis of symmetry of the transducer housing) is known at all times, as is the timing of each transmitted pulse. Thus, every time a transmitted pulse is emitted, the exact position of the transducer head relative to a known reference is always known with precision and accuracy. Thus, the timing of every reflected pulse captured by the transducer can be correlated with the eye surface of interest. For a compound scanning head that can perform sector scans at in any of several planes with respect to the plane of the arc track and do so at many positions along an arc track, the accurate and precise time and position information so obtained can be used to construct an image of a three dimensional object such as a lens.

Measuring Acoustic Velocities of Eye Components

Figure 20:
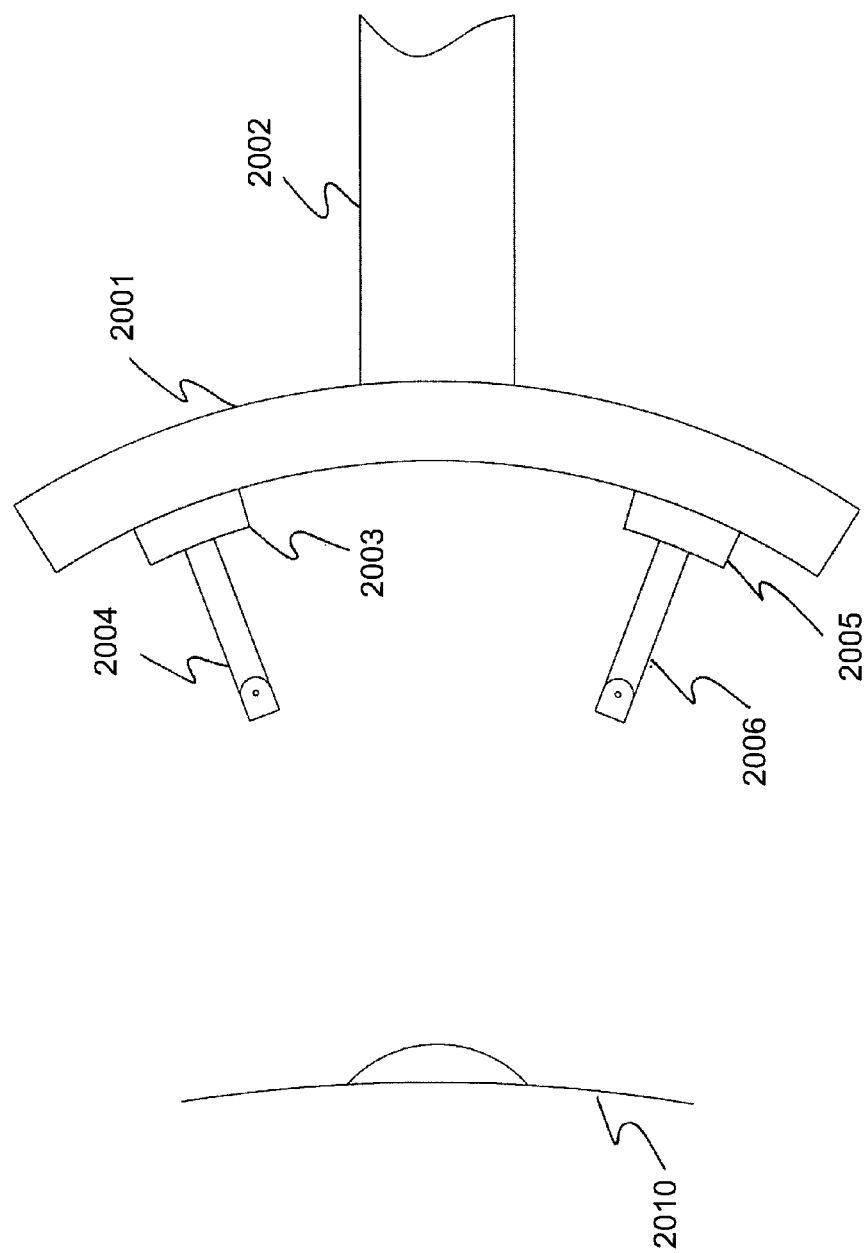
FIG. 20 is a schematic of a dual carriage scanner.

FIG. 20 is a schematic side view of a dual carriage scanner. This figure shows a scan head positioning arm 2002 and arc guide track assembly 2001 on which two transducer carriages 2003 and 2005 are shown along with their respective transmitter/receiver ultrasonic transducers 2004 and 2006. The transducers are both aimed at approximately the center of curvature of an eye component 2010. Each transducer can be operated independently, for example, with each covering half of the arc track guide and both together producing a total eye image. This would have the advantage of reducing scan time in half. The transmitter/receiver transducer heads may be fixed as in a conventional arc scanner or they may be rotatable as in a compound head scanner described previously.

This configuration can also be used to measure the acoustic velocity of various eye tissues. The acoustic pulses emitted by a transducer reflect off various eye tissue interfaces and the reflected pulses are received by the transducer as described in "Ultrasonography of the Eye and Orbit" cited previously. These are received as waveforms of amplitude versus time. An acoustic velocity must be used to translate time differences into distances to construct an image. Typically, the acoustic velocity of water at 37 degrees C is used. This gives minimal errors for surfaces and layers within the cornea. However, accurate placement of lens components will require correction for the acoustic velocity of the aqueous humor (between the cornea and lens) and for the acoustic velocity inside the lens. A single transducer cannot measure the acoustic velocity in the lens since both lens acoustic velocity and lens surface locations are unknown. The dual transducers, shown in FIG. 20, can however determine both. For example, one of the transducers can be set at the center of the arc guide track at the zero reference angle so that an acoustic pulse is emitted along the optical axis. This gives a first transit time through any eye component. Then one transducer can be set at an angle a above the 0 degree reference angle while the other transducer is set at an angle minus a below the 0 degree reference angle. Both transducers would be aimed at the same point along the optical axis on the surface of interest as the transducer used to measure the first transit time. The acoustic pulse from one transducer will reflect from the surface of interest and be received by the second transducer. This gives a second transit time through the eye component. This procedure will be described with reference to FIG. 21 to illustrate how the acoustic velocity in, for example, the lens can be determined.

The accepted acoustic velocities for various eye components, at 37 C, are:
cornea~1,639 m/s
aqueous humour~1,532 m/s
sclera~1,622 m/s
lens~1,641 m/s
cataractous lens~1,629 m/s These values are from Table 1.1 of "Ultrasonography of the Eye and Orbit" cited previously. For comparison, the acoustic velocity (also known as the speed of sound) in water at 37 C is ~1,520 m/s. As can be seen, the lens velocities are higher than that of water and so there can be significant positional errors when determining the spatial location of the posterior lens surface.

Figure 21:
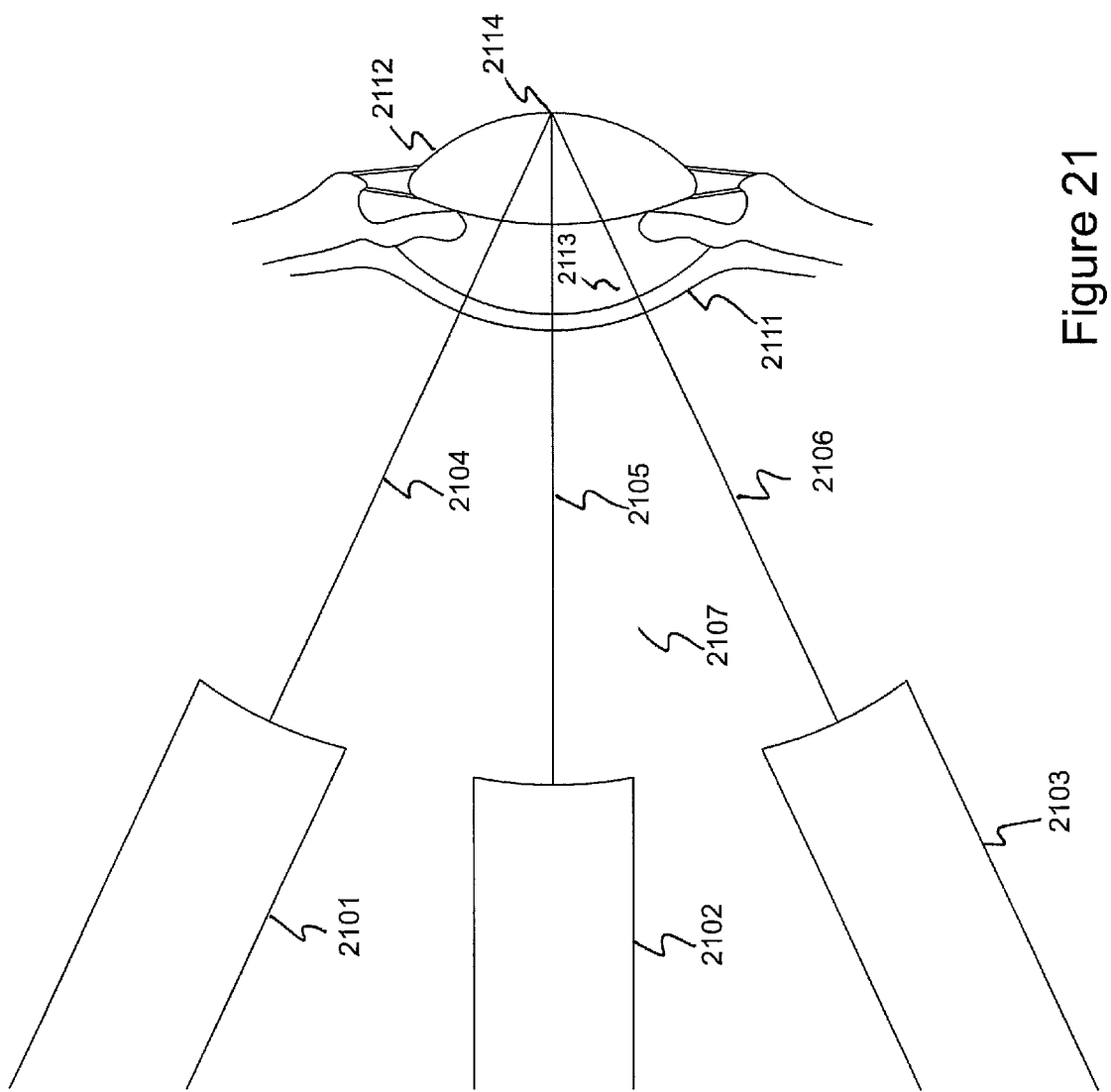
FIG. 21 shows how the acoustic velocity of a lens can be determined.

FIG. 21 shows how the acoustic velocity of a lens can be determined. The acoustic pulses emitted by a transducer must first pass through water and then through the various tissues of the eye. Similarly, the reflected pulses must pass back through water to be received by the transducer after leaving the eye. The water path used in an arc scanner is described in detail in U.S. patent application Ser. No. 12/347,674. In FIG. 21, it is assumed, for purposes of this illustration, that the acoustic velocities of water 2107, the corneal fluid 2111 and the aqueous humor 2113 are known. If these are known, then the location of the anterior and posterior cornea surfaces and the anterior surface of the lens can be determined with accuracy. One of the transducers 2102 can be used to obtain a first transit time $\Delta t_1$, through the lens along the axis which will produce a reflection from point 2114 on the posterior surface of the lens 2112. The distance between the anterior and posterior lens surfaces along the optical axis is:

$$(x_2 - x_1) = \Delta t_1 \, c_{lens}$$

where $x_2$, is the point 2114, $x_1$ is a known point on the anterior lens surface and $c_{lens}$ is the acoustic velocity of the lens fluid.

Next, transducer 2101 can be used to emit an acoustic pulse to reflect from the posterior surface of the lens at point 2114 and transducer 2103 can be used to receive the reflected pulse. This gives a second transit time $\Delta t_2$ through the lens along ray 2104 and back along ray 2106. The distance along this path between the anterior and posterior lens surfaces is:

$$(x_3 - X_2) = \Delta t_2 \, c_{lens}$$

where $x_2$ is the point 2114, $x_3$ is a known point on the anterior lens surface and $c_{lens}$ is the acoustic velocity of the lens fluid. Thus there are two equations in the two unknowns $x_2$ and $c_{lens}$ which can be solved for the location of point 2114 and the average acoustic velocity of the lens fluid.

This same procedure can be used to find the acoustic velocity of the corneal fluid, the aqueous humor and the iris and so the assumptions made for the example of the lens acoustic velocity determination can be fulfilled.

High Frequency Ultrasound Tomography

Figure 22:
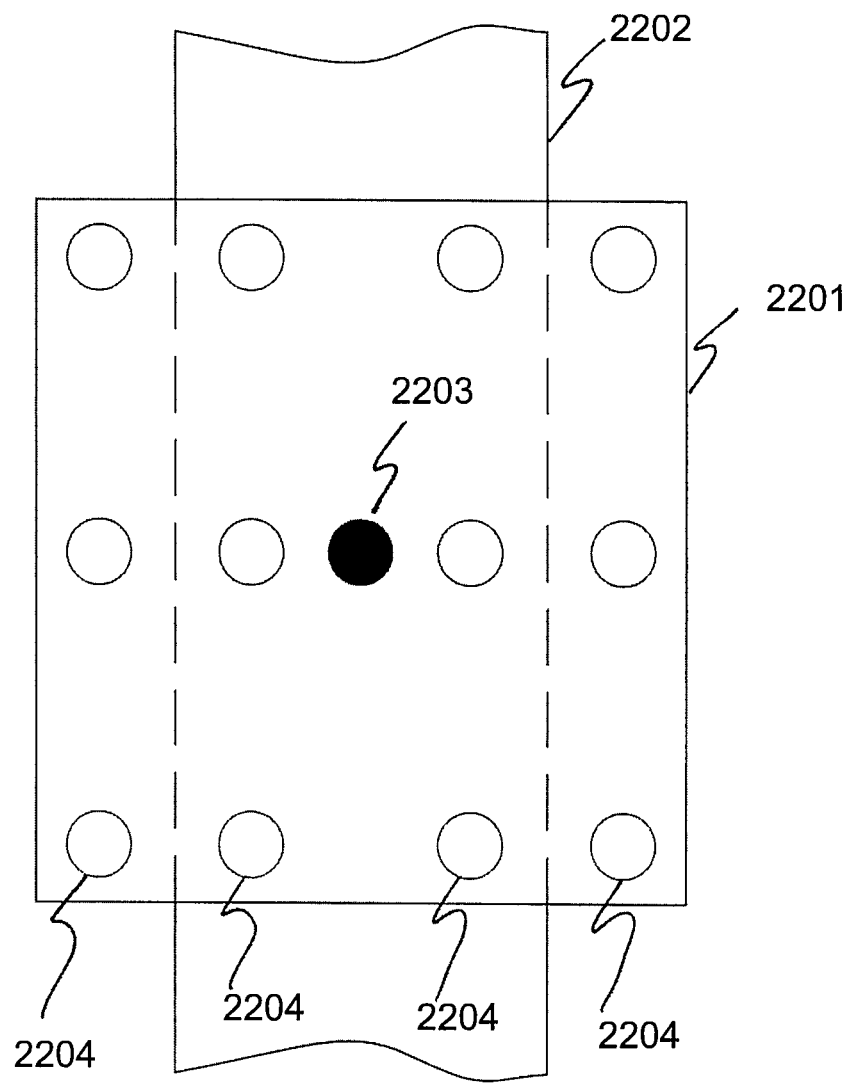
FIG. 22 is a schematic of a carriage for multiple transducers.

Another mode of operation is described in FIG. 22. This is a tomographic mode and requires a substantially different scanner configuration that a scanner with a single transducer.

In arc scanning, sector scanning or compound scanning as described previously, there is typically a single transducer which both generates acoustic pulses and receives the reflected acoustic pulses. To receive a reflected pulse, the transmitted pulse wave front must arrive approximately normally to the surface being imaged in order for there to be sufficient energy in the reflected pulse for a coherent signal (sufficiently higher than the background noise) to be captured by the transducer.

In tomography, there may be a single transmitter source and an array of receivers. The receivers are placed at some distance from the source. Any one of the receivers may pick up a reflected acoustic pulse. The spacing between the transmitter and receiver and the timing between the transmitted and received pulse may be used along with known acoustic velocities in the transmission media to deduce the location and thickness of layers such as for example in delineating an oil or gas deposit.

FIG. 22 is a schematic plan view of a carriage for multiple transducers. In the example shown, a carriage assembly 2201 is shown in plan view on an arc guide track 2202. A transmitter/receiver transducer is shown mounted in this example in the center of the carriage. A number of ultrasonic receiver transducers are shown arrayed around the ultrasonic transmitter/receiver transducer. It can be seen that the transmitter/receiver transducers can be pulsed while all the receiver transducers and the transmitter/receiver transducer can listen for reflected pulses. For example, if two such carriage assemblies are used, one carriage can be positioned on the one side of the arc track guide and a second carriage can be moved back and forth along the remaining track of the arc guide track. When one transmitter/receiver transducer is pulsed, all the receiver transducers can receive reflected pulses. This sequence is defined herein as a pulse event. Since the acoustic velocity of transmitted and reflected pulses is essentially constant in water, the cornea, the lens and in the aqueous humor of the eye; since the location of both transmitter/receiver transducers and all the receiver transducers are known precisely; and since the timing of the transmitted pulses are accurately known, it is possible to construct the position of all acoustically reflecting surfaces from a number of pulse events. When these are plotted, they will form a three-dimensional grid of points that can be used to define the various reflecting surfaces. This is a simpler version of tomography than for example used in oil prospecting since the acoustic velocities of all the eye components and transmission media are all the same, approximately constant and well known. As can be appreciated, the guide track need not be a circularly curved guide track but can be a guide track with a different curvature or even a linear track.

Volume of a Natural or Artificial Lens

Figure 23:
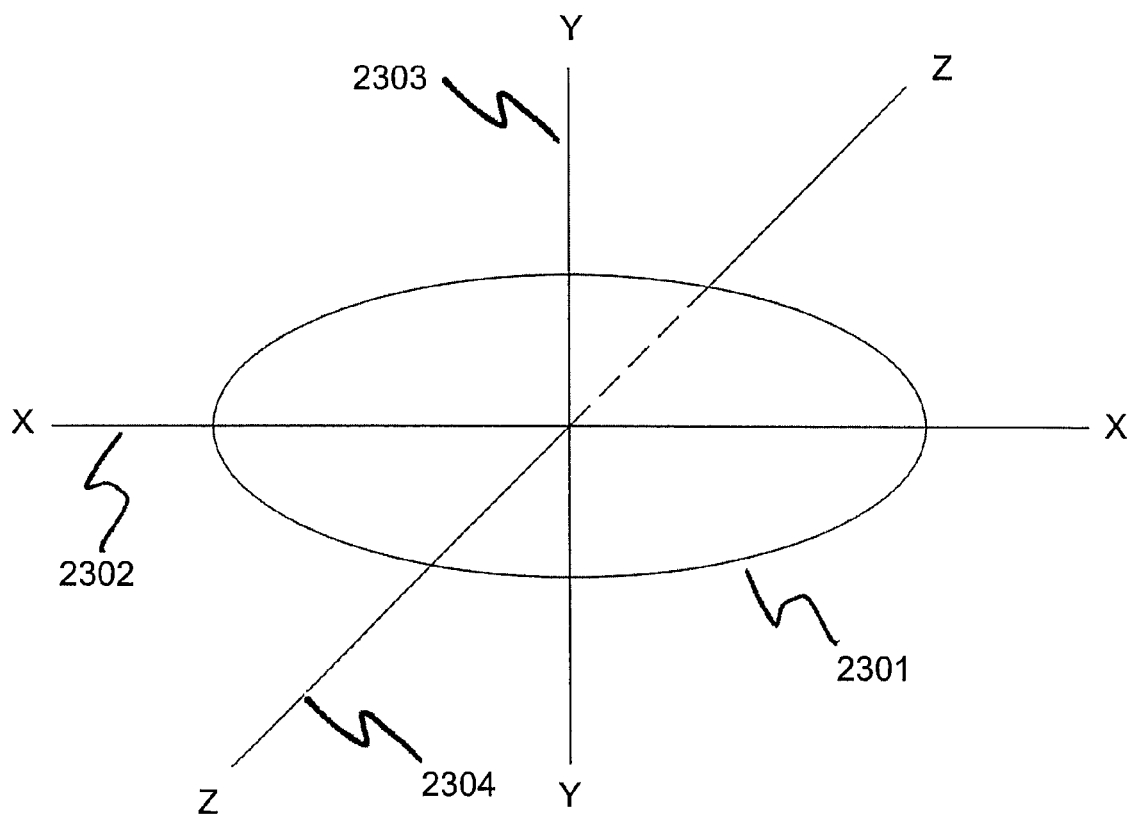
FIG. 23 shows a cross-sectional view of a human crystalline lens.

FIG. 23 is a cross-sectional view of a natural lens. The lens has an ellipsoid, biconvex shape. In an adult, the lens has an axial or horizontal length of approximately 9 millimeters (nasal side to temporal side). This is the length along the x-axis of FIG. 23. The lens has a thickness of approximately 3.5 millimeters. This is the thickness along the z-axis of FIG.

23. The lens has a height of approximately 3.5 millimeters. This is the height along the y-axis of FIG. 23.

If the lens is approximately symmetrical about all three axes, then its volume can be approximated as an ellipsoid with the approximate volume of the lens being given by:

lens volume=$4/3\pi$ a b c where a=the lens half width (major equatorial radius)
b=the lens half height (polar radius)
c=the lens half thickness (minor equatorial radius)

The lens is not necessarily symmetric about the x-axis and so the volume computational method described in FIG. 23 should give a more accurate volume of the lens capsule than an ellipsoid volume approximation.

Figure 24:
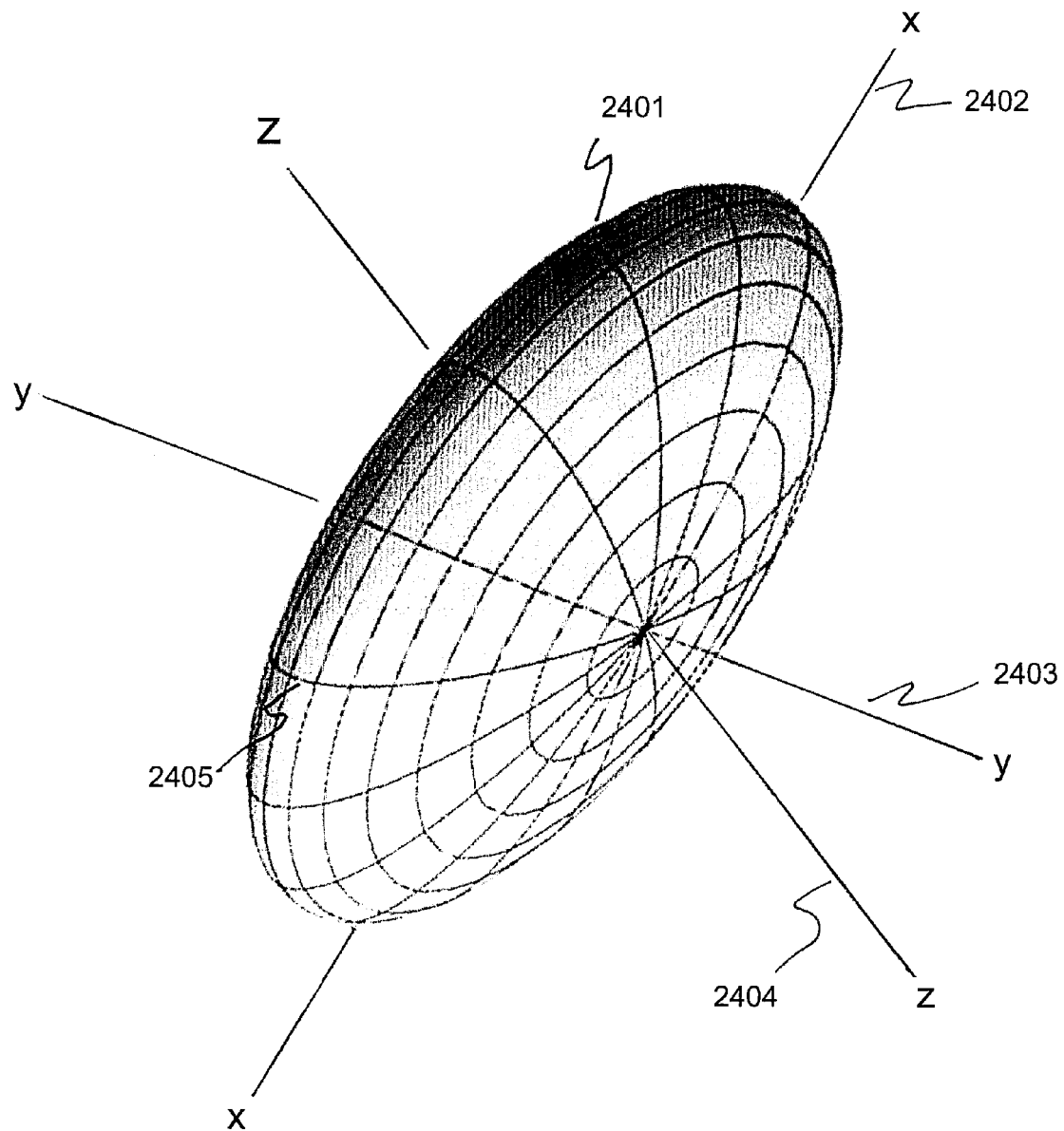
FIG. 24 is a schematic of a lens showing a wire frame grid.

FIG. 24 is a schematic of a lens showing a wire frame grid defining the surface of the lens. This figure shows an isometric view of a lens 2401 where the x-axis 2402 is the major horizontal axis of the lens and passes through the geometric center of the lens. The length of the lens is defined along the x-axis 2402. The y-axis 2403 is the vertical and also passes through the geometric center of the lens. The lens thickness is defined along the z-axis 2404 which also passes through the geometric center of the lens. The surface of the lens 2401 can be defined by a series of contour lines 2405 that can be generated by imaging methods that are possible using a compound scanning head of the present invention or by the tomographic methods generated by the configuration of the invention illustrated by FIG. 22.

Once a wire frame surface grid is constructed, other points on the lens surface can be approximated by any number of well-known multi-dimensional interpolation methods. The co-ordinates can be used to compute the volume of the lens, for example, if the lens is not a perfect ellipsoid.

Implantation of Artificial Lenses

In a natural or crystalline lens, zonules connect the lens with the ciliary body. As the ciliary muscle expands or contracts, the lens responds since it is connected to the ciliary muscle by the zonules as illustrated for example in FIG. 3.

In a lens replacement, the zonules are detached and are usually damaged and rendered inoperative by the replacement procedure. Therefore artificial accommodating lenses, typically require alternate means of attachment or alternate means to allow them to accommodate in response to the ciliary muscle. For example, some accommodating lenses may have haptics attached to the lens (approximately where the zonules were attached) and these may be designed to be inserted into the sulcus. The action of the ciliary muscle causes the haptics, which act as hinges, to change shape in such as way as to compress and thicken the lens, allowing it to provide an accommodating action. Other accommodating lenses may not have attaching mechanisms but may rely on increased pressure in the vitreous humour to move the lens slightly forward, thereby causing an accommodating action. Other methods for restoring accommodative action in a natural lens include injections which tend to soften the lens so as to restore its natural accommodating action.

An arc scanner with a compound head or an arc scanner operated in tomographic mode can be used to help restore the natural lens or help to implant an accommodating lenses as well as confirm proper operation when a lens is restored or an accommodating lens is implanted.

For example, such a scanner can be used to determine the axial width (along the z-axis of FIG. 23) of the patient's natural lens so that an accommodating lens of the approximate correct width can be selected. Further, such a scanner can be used to determine the volume of the patient's natural lens so that an accommodating lens of the approximate correct volume can be selected.

A number of variations and modifications of the inventions can be used. As will be appreciated, it would be possible to provide for some features of the inventions without providing others. For example, though the embodiments are discussed with reference to an arc scanning device, it is to be understood that the various embodiments may be used with other types of acoustic scanning devices using different transducer motion strategies.

The present invention, in various embodiments, includes components, methods, processes, systems and/or apparatus substantially as depicted and described herein, including various embodiments, sub-combinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, for example for improving performance, achieving ease and/or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover though the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. An ultrasound eye imaging system to image a portion of a patient's eye, comprising:

a positioning mechanism;

a scan head attached to the positioning mechanism, the scan head comprised of at least an arcuate guide track and a transducer carriage that moves back and forth along the arcuate guide track;

an eyepiece which maintains the patient in a fixed location with respect to the arcuate guide track;

a transducer housing whose proximal end is mounted on the transducer carriage such that an axis of rotation of the transducer housing is aligned along a radius of curvature of the arcuate guide track; and an ultrasound transducer attached to the distal end of the transducer housing wherein the ultrasound transducer can rotate about a fixed point on the distal end of the transducer housing;

wherein an ultrasound pulse is emitted by the ultrasound transducer along a direction perpendicular to an emitting face of the ultrasound transducer at a selected angle with respect to the axis of rotation of the transducer housing and in a plane defined by the arcuate guide track and its center of curvature.

2. The system of claim 1, wherein a position and orientation in space of the face of the ultrasound transducer is known at any time when the ultrasound pulse is emitted.

3. The system of claim 1, wherein the portion of the eye imaged is one or more of a surface or layer of a cornea, a surface of a lens, a zonule, a region of a sclera, a region of a ciliary body, an iris and a ciliary sulcus.

4. The system of claim 1, wherein the ultrasound pulse emitted by the ultrasound transducer is configured to allow an image to be formed of a portion of a posterior surface of the eye.

5. The system of claim 1, wherein the ultrasound transducer can rotate in a plane defined by the arcuate guide track and its center of curvature.

6. A method of forming an ultrasound image of a portion of an eye, comprising:
(a) positioning a scan head with respect to a patient's eye;
(b) moving a transducer carriage along an arcuate guide track, the transducer carriage configured with a transducer housing whose proximal end is mounted on the transducer carriage such that the axis of rotation of the transducer housing is aligned along a radius of curvature of the arcuate guide track, wherein an eyepiece maintains the patient in a fixed location with respect to the arcuate guide track;
(c) rotating an ultrasound transducer attached to the distal end of the transducer housing about a fixed point at a selected angle with respect to the axis of the transducer housing;
(d) emitting an ultrasound pulse by the ultrasound transducer along a direction perpendicular to an emitting face of the transducer at selected times;
(e) determining the location and orientation in space of the emitting face of the ultrasound transducer at a time the ultrasound pulse is emitted; and
(f) forming an image of the portion of the eye from a plurality of reflected pulses received by the ultrasound transducer.

7. The method of claim 6, wherein determining timing of emitted pulses, determining the position and orientation of the emitting face of the ultrasound transducer, and the forming the image of the portion of the eye from a plurality of reflected pulses is carried out by a computer.

8. The method claim 6, wherein the portion of the eye imaged is one or more of a surface or layer of a cornea, a surface of a lens, a zonule, a region of a sclera, a region of a ciliary body, an iris and a ciliary sulcus.

9. The method of claim 6, wherein the ultrasound pulse emitted by the ultrasound transducer is configured to allow an image to be formed of a portion of a posterior surface of the eye.

10. The method of claim 6, wherein the ultrasound transducer rotates back and forth in a plane defined by the arcuate guide track and its center of curvature.

* * * * *